United States Patent [19]

Umezawa et al.

[11] Patent Number: 4,472,304

[45] Date of Patent: Sep. 18, 1984

[54] (AMIDO)N-SUBSTITUTED BLEOMYCINS, SALTS THEREOF AND PROCESS FOR PREPARATION THEREOF

[75] Inventors: Hamao Umezawa, Tokyo; Akio Fujii, Kamakura; Yasuhiko Muraoka, Kitamoto; Tokuji Nakatani, Saitama; Takeyo Fukuoka, Yono; Katsutoshi Takahashi, Tokyo, all of Japan

[73] Assignee: Nippon Kayaku Kabushiki Kaisha, Tokyo, Japan

[21] Appl. No.: 451,437

[22] Filed: Dec. 20, 1982

[30] Foreign Application Priority Data

Dec. 29, 1981 [JP] Japan .................. 56-210447

[51] Int. Cl.³ .......................................... C07C 103/52
[52] U.S. Cl. .......................................... 260/112.5 R
[58] Field of Search ................................ 260/112.5 R

[56]  References Cited

U.S. PATENT DOCUMENTS

| | | | |
|---|---|---|---|
| Re. 30,413 | 10/1980 | Umezawa et al. | 260/112.5 R |
| Re. 30,451 | 12/1980 | Umezawa et al. | 260/112.5 R |
| 3,846,400 | 11/1974 | Umezawa et al. | 260/112.5 R |
| 3,932,374 | 1/1976 | Umezawa et al. | 260/112.5 R |
| 4,267,102 | 5/1981 | Fujii et al. | 260/112.5 R |
| 4,315,851 | 2/1982 | Yoshikumi et al. | 260/112 R |
| 4,326,054 | 4/1982 | Umezawa et al. | 260/112.5 R |
| 4,339,426 | 7/1982 | Meares et al. | 260/112.5 R |

Primary Examiner—Delbert R. Phillips
Attorney, Agent, or Firm—Banner, Birch, McKie & Beckett

[57] ABSTRACT

A promising carcinostatic (amido)N-substituted bleomycin represented by the following formula, or a salt thereof and a process for the preparation thereof:

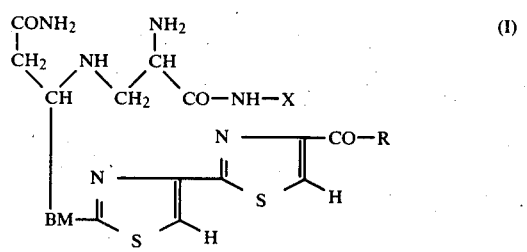

wherein BM represents a moiety of bleomycin skeleton; X represents an alkyl of 1 to 18 carbon atoms, an aminoalkyl of 1 to 12 carbon atoms, a lower alkyl having a halogen, phenyl indolyl, 5- or 6-membered heterocyclic group, or (lower)alkylamino (the alkyl group may have a substituent group) as a substituent, naphthyl, thiazolyl, or N-phenyl(lower)alkylpiperazinyl; and R represents a terminal amino residue of the bleomycin.

12 Claims, No Drawings

(AMIDO)N-SUBSTITUTED BLEOMYCINS, SALTS THEREOF AND PROCESS FOR PREPARATION THEREOF

This invention relates to novel (amido)N-substituted bleomycins, salts thereof and a process for the preparation thereof.

Bleomycin is a family of carcinostatic antibiotic substances discovered in 1966 by Umezawa, one of the present inventors, and collaborators [Journal of Antibiotics, 19A, p. 200 (1966)]. It is produced by *Streptomyces verticillus*, an Actinomycete, and is a basic water-soluble glycopeptide capable of readily chelating one atom of divalent copper. In ordinary culture, 16 members of the bleomycin family are produced and are each isolated [e.g., Umezawa et al., Journal of Antibiotics, 19A, p. 210 (1966)]. Of these bleomycins, $A_1$, $A_2$, $A_5$, $B_2$ and demethyl-$A_2$ are currently being widely used in the form of copper-free mixture (hereinafter referred to as bleomycin complex) in clinical fields of cancer therapy; more particularly, they are successfully used in the treatment of squamous cell carcinoma as major target, skin cancer, head and neck cancer, lung cancer, and malignant lymphoma. Various bleomycins are also disclosed in U.S. Pat. No. 3,922,262 and U.S. Pat. No. Re 30,451.

The bleomycins are generally produced in copper-containing form in the ordinary fermentation. The copper-free form is obtained by removing the copper from the copper-containing form. The term "bleomycin", as herein employed, includes both the copper-containing and the copper-free forms, unless specifically indicated.

The bleomycins are represented by the general formula (II)

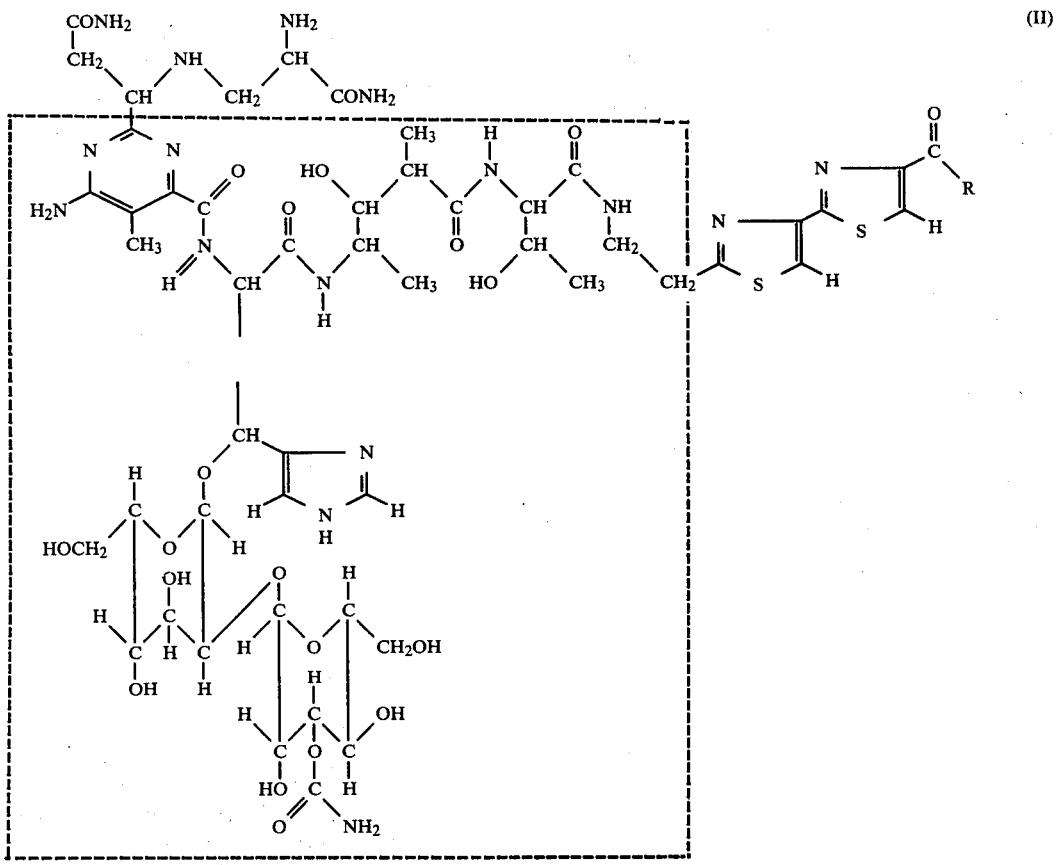

wherein R is a terminal amine residue of bleomycin; and the chelated copper is omitted in the case of copper-containing form.

It was found, however, that the bleomycins are inactivated by the action of a bleomycin-inactivating enzyme [hereinafter referred to briefly as inactivating enzyme; Umezawa et al., Journal of Antibiotics, Vol. 27, p. 419 (1974)]. It was further found that the bleomycins are relatively less inactivated in the skin and lung where they exhibit a high activity, while they are easily inactivated in the stomach where they have been believed to exhibit no action and that such an inactivation phenomenon is less marked in the squamous cell carcinoma in mouse than in the sarcoma in mouse, both of which are induced by 20-methylcholanthrene [Umezawa et al., journal of Antibiotics, Vol. 25, p. 409 (1972); Vol. 27, p. 419 (1974)]. Furthermore, it was found that the bleomycin-inactivating action is exhibited by the squamous cell carcinoma in human head and neck, especially by those of the low differentiation type against which the bleomycins have been believed to be not so effective [Mueller et al., Cancer, Vol. 40, p. 2787 (1977)].

As is understandable from the above reports, the bleomycins are incapable of exhibiting a sufficient activity against carcinomas containing bleomycin-inactivating enzyme of high activity. This is one of the reasons for the need of further improvement in bleomycins. The present inventors contemplated that if it is possible to discover a bleomycin derivative difficulty susceptible to enzymatic inactivation, it would become possible to treat more effectively, for example, head and neck cancer, esophagus cancer, lung cancer, and squamous cell carcinomas in other regions and to treat those adenocarcinomas such as gastric cancer which are not responsive to the treatment with conventional bleomycins. From such a viewpoint the present inventors made an extensive study and, as a result, found that the bleomycins are inactivated to a lesser degree when a substituent (-X) is introduced to the nitrogen atom in amide linkage of the partial structure, 2,3-diaminopropanamide

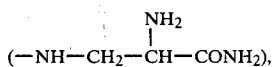

of bleomycins. The present invention is based on this finding.

The primary object of this invention is to provide novel bleomycins which are difficulty inactivated by the inactivating enzyme and to provide a process for the preparation thereof.

Other objects and advantages of this invention will become apparent from the following description.

According to this invention there are provided (amido)N-substituted bleomycins or salts thereof, intermediates for the preparation thereof, and a process for the preparation thereof, said (amido)N-substituted bleomycins being represented by the general formula

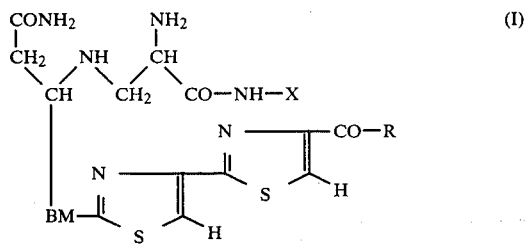

wherein BM represents a moiety of bleomycin skeleton; X represents (1) an alkyl of 1 to 18 carbon atoms, (2) an aminoalkyl of 1 to 12 carbon atoms, (3) a lower alkyl having as substitutent (a) 1 to 3 halogen atoms, (b) 1 or 2 phenyl groups, (c) an indolyl group, or (d) a 5- or 6-membered heterocyclic group containing an oxygen, sulfur or nitrogen atom (among the substituent groups, the phenyl or indolyl group may be further substituted by a halogen atom or a lower alkoxy group), (4) $X_1$-(lower)alkyl [where $X_1$ is

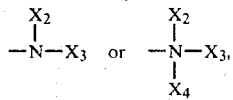

$X_2$ is a hydrogen atom, a lower alkyl or benzyl, $X_3$ is (a) a lower alkyl, (b) a phenyl(lower)alkyl, or (c) a mono- or di-(lower)alkylamino(lower)alkyl which may be substituted by a phenyl or halophenyl group, $X_4$ is (a) a lower alkyl or (b) a phenyl(lower)alkyl] (5) naphthyl, (6) thiazolyl, or (7) an N-phenyl(lower)alkylpiperazinyl; and R represents a terminal amino residue of the bleomycin.

The moiety of bleomycin skeleton represented by BM is the portion of a bleomycin molecule enclosed in dotted lines in the general formula (II) of bleomycins and includes both the copper-containing form and the copper-free form, unless specifically indicated. The lower alkyls are alkyls of 1 to 6 carbon atoms, such as methyl, ethyl, n-propyl, isopropyl, n-butyl, isobutyl, n-penthyl, 3-methylbutyl, 3-methylpentyl, and n-hexyl.

Examples of individual groups represented by X in the general formula (I) are as follows:

(1) Alkyls of 1 to 18 carbon atoms: methyl, ethyl, n-propyl, isopropyl, n-butyl, isobutyl, tert-butyl, n-pentyl, 3-methylbutyl, neopentyl, n-heptyl, 3-methylpentyl, n-hexyl, 1,5-dimethylhexyl, isohexyl, n-octyl, n-decyl, lauryl, myristyl, cetyl, and stearyl.

(2) Aminoalkyls of 2 to 12 carbon atoms: 2-aminoethyl, 3-aminopropyl, 4-aminobutyl, 6-aminohexyl, 12-aminododecyl, and 4-amino-4-methyl-1-dimethylpentyl.

(3) Lower alkyls having as substituent (a) 1 to 3 halogen atoms, (b) 1 or 2 phenyl groups, (c) an indolyl group, or (d) a 5- or 6-membered heterocyclic group containing an oxygen, sulfur or nitrogen atom (among the substituent groups, the phenyl or indolyl group may be further substituted by a halogen atom or a lower alkoxy group): 2,2,2-trifluoroethyl, 2,2,2-trichloroethyl, 2,2-difluoroethyl, 2,2-dichloroethyl, benzyl, diphenylmethyl, 2-phenylethyl, 2,2-diphenylethyl, 1-phenylethyl, 1,2-diphenylethyl, 3-phenylpropyl, 2-phenylisopropyl, 1,3-diphenylpropyl, 3,3-diphenylpropyl, 4-phenylbutyl, 4,4-diphenylbutyl, chlorobenzyl, dichlorobenzyl, bromobenzyl, methoxybenzyl, dimethoxybenzyl, ethoxybenzyl, methylenedioxybenzyl, propoxybenzyl, p-chlorophenylethyl, p-methoxyphenylethyl, p-benzyloxybenzyl, furylmethyl, 2-furylethyl, 2-thiazolylmethyl, 2-pyrazolylmethyl, 2-imidazolylmethyl, 4-imidazolylmethyl, 2-thienylmethyl, 2-pyridylmethyl, 3-pyridylmethyl, 4-pyridylmethyl, 3-indolylmethyl, 2-(3-indolyl)ethyl, 4-methoxy-3-indolylmethyl, 2-pyrimidylmethyl, 2-pyrimidylethyl, 4-pyrimidylmethyl, 4-pyrimidylethyl, 2-piperidylmethyl, 3-piperidylmethyl, 4-piperidylmethyl, 2-(2-piperidyl)ethyl, 2-(3-piperidyl)ethyl, 2-(4-piperidyl)ethyl, 1-(2-piperidyl)ethyl, 1-(3-piperidyl)ethyl, 1-(4-piperidyl)ethyl, 2-(piperidino)ethyl, 2-piperazylmethyl, 2-(2-piperazylethyl), 2-(piperidino)ethyl, 3-piperidinopropyl, 2-(morpholino)ethyl, 3-(morphilino)propyl, 2-morpholinylmethyl, 3-morpholinylmethyl, 2-(morpholinyl)ethyl, and 3-(morpholinyl)propyl.

(4) $X_1$-(lower)alkyls (where $X_1$ is

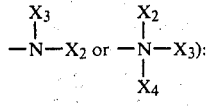

dimethylaminoehtyl, diethylaminoethyl, dipropylaminoethyl, propylaminoethyl, dimethylaminopropyl, diethylaminopropyl, dipropylaminopropyl, propylaminopropyl, dibutylaminopropyl, butylaminopropyl, benzylaminopropyl, 2-phenylethylaminopropyl, 1-phenylethylaminopropyl, 3-phenylpropylaminopropyl, 4-phenylbutylaminopropyl, methylaminoethylaminopropyl, ethylaminopropylaminopropyl, propylaminopropylaminopropyl, butylaminopropylaminopropyl, N-(butylaminopropyl)-N-methylaminopropyl, dibutylaminopropylaminopropyl, penthylaminopropylaminopropyl, ethylaminobutylaminopropyl, propylaminobutylaminopropyl, ethylaminopropylaminobutyl, butylaminopropylaminobutyl, benzylaminoethyl aminoethyl, benzylaminoethylaminopropyl, benzylaminopropylaminopropyl, benzylaminobutylaminopropyl, phenylethylaminopropylaminopropyl, N-(phenylethylaminopropyl)-N-methylaminopropyl, N-(chlorobenzylaminopropyl)-N-methylpropyl, N-(bromobenzylaminopropyl)-N-methylpropyl, N-(chlorophenylethylaminopropyl)-N-methylpropyl, benzylaminopropyl-N,N-dimethylaminopropyl, dibenzylaminopropyl-N,N-diethylaminopropyl, and dibenzylaminopropyl-N-methyl-N-benzylaminopropyl.

(5) Naphthyls: α-naphthyl and β-naphthyl.
(6) Thiazolyls: 2-thiazolyl, 3-thiazolyl, and 4-thiazolyl.
(7) N-Phenyl(lower)alkylpiperidyls: N-benzyl-4-piperidyl, N-phenylethyl-4-piperidyl, N-benzyl-3-piperidyl, and N-benzyl-2-piperidyl.

The terminal amino residue of bleomycins represented by R may be any of the substituted or unsubstituted aliphatic amino groups, but it is usually an aliphatic primary amino group of basic nature represented by the general formula (III)

$$R_2-R_1-NH- \quad\quad (III)$$

wherein $R_1$ is (1) a chain of alkylene groups which may have a nitrogen atom intervened between alkylene groups in the chain [examples of such a group are those represented by the formulas $-R_{12}-Y_1-R_{13}-$ and $-R_{12}-Y_1-R_{13}-Y_2-R_{14}-$, wherein $R_{12}$, $R_{13}$ and $R_{14}$ are alkylene groups and $Y_1$ and $Y_2$ are each a group of the formula

(where $R_3$ and $R_4$ are hydrogen atoms or lower alkyls which may have substituents)], (2)

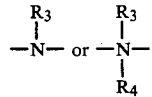

or (3) phenylene; and $R_2$ is any of the groups of basic nature [examples of such a group are those represented by the formula

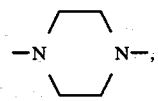

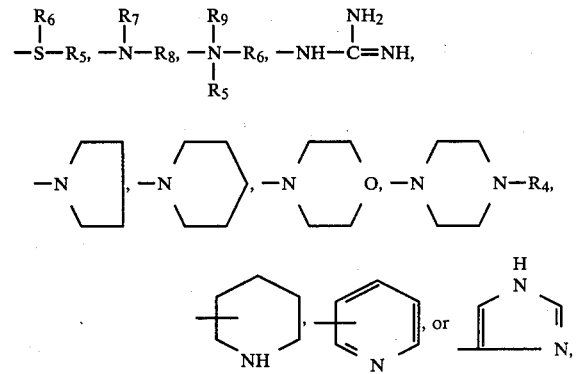

wherein $R_4$ is as defined above; $R_5$, $R_6$ and $R_9$ are each a lower alkyl which may have a substituent; and $R_7$ and $R_8$ are each a hydrogen atom or an alkyl of 1 to 10 carbon atoms which may have a substituent]. The alkyl-ene of the above amino group is that of 1 to 8 carbon atoms such as, for example, $-CH_2-$, $-(CH_2)_2-$,

$-(CH_2)_3-$,

$-(CH_2)_4-$, $-(CH_2)_5-$, $-(CH_2)_6-$, and $-(CH_2)_8-$, though the alkylenes having 2 to 4 carbon atoms are most frequently used. The substituents on the above alkyl groups include hydroxyl, alkoxy (for example, methoxy, ethoxy, propoxy and butoxy), phenyl [which may have one or more substituents selected from halogens, cyano, lower alkyls, benzyloxy, and substituted (e.g. alkoxy-, phenoxy-, or halogen-substituted) benzyloxy groups], and cycloalkyls of 5 to 13 carbon atoms.

Examples of the above amino groups are 2-aminoethylamino, 3-aminopropylamino, 2-dimethylaminoethylamino, 2-diethylaminoethylamino, 3-dimethylaminopropylamino, 3-diethylaminopropylamino, 3-(3-butylaminopropylamino)propylamino, 3-(2-oxypropylamino)propylamino, 3-piperidinopropylamino, 3-(1-phenylethylamino)propylamino, 2-aminopropylamino, 3-methylaminopropylamino, 3-butylaminopropylamino, 3-(6-aminohexylamino)propylamino, 3-trimethylaminopropylamino, 3-(3-dimethylaminopropylamino)propylamino, 3-(3-aminopropylamino)propylamino, 3-[N-methyl-N-(3-aminopropyl)amino]propylamino, 3-pyrrolidinylpropylamino, 3-piperidinylpropylamino, 3-morpholinopropylamino, 3-piperazinylpropylamino, 3-[4-(3-aminopropylpiperazinyl)]propylamino, 3-(3-pyrrolidinylpropylamino)propylamino, 3-(3-piperdinylpropylamino)propylamino, 3-(3-morpholinylpropylamino)propylamino, 3-(3-oxypropylamino)propylamino, 3-(3-methoxypropylamino)propylamino, 3-benzylaminopropylamino, m-aminomethylbenzylamino, p-aminomethylbenzylamino, 2-cyclopentylaminoethylamino, 3-cyclohexylaminopropylamino, 4-cyclohexylaminobutylamino, cycloheptylaminopropylamino, 3-cyclooctylaminopropylamino, 3-[N-methyl-N-(3-cyclooctyl methylaminopropyl)amino]-propylamino, 3-cyclodecanylmethylaminopropylamino, 3-{N-methyl-N-[3-(2-p-chlorophenylethylamino)propyl]amino}propylamino, 3-{N-methyl-N-[3-(m,p-dibenzyloxybenzyl)aminopropyl]amino}propylamino, 3-{N-methyl-N-[3-(p-cyanobenzylamino)propyl]amino}propylamino, 3-{N-methyl-N-[3-(cycloundecanylmethylamino)propyl]amino}propylamino, 3-{N-methyl-N-[bis(m,p-dibenzyloxybenzyl)aminopropyl]amino}propylamino, 3-{N,N-dimethyl-N-[3-(dibenzylamino)propyl]amino}propylamino, 3-{N,N-diethyl-N-[3-(dibenzylaminopropyl)]amino}propylamino, 3-{N,N-dimethyl-N-[3-(N,N-dimethyl-N-(3-dibenzylaminopropyl)amino)propyl]amino}propylamino, 3-{N,N-dimethyl-N-[3-(N,N-dimethyl-N-(3-cyclooctylmethylaminopropyl)amino)propyl]amino}propylamino, 3-[4-(3-dibenzylaminopropyl)-piperidyl]propylamino, and 3-{4-[3-(cyclooctylmethylamino)propyl]piperidyl}propylamino.

As desirable compounds, mention may bemade of those in which R is 3-[(S)-1'-phenylethyl]aminopropylamino or 3'-(n-butylaminopropyl)aminopropylamino and those having an amine residue representea by the formula (IV)

$$-NH-(CH_2)_3-A-(CH_2)_3-B \quad (IV)$$

wherein A is

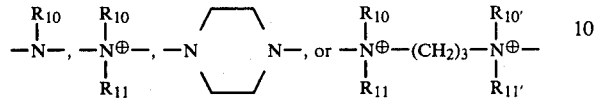

(where $R_{10}$, $R_{10}'$, $R_{11}$ and $R_{11}'$, which may be the same or different, are each a lower alkyl, benzyl, or a halogen-substituted benzyl) and B is

[where $R_{12}$ is (1) a phenyl(lower)alkyl, (2) a phenyl(lower)alkyl having on the phenyl nucleus one or more substitutents selected from (a) halogens, (b) lower alkyls, (c) lower alkoxys, (d) cyano, (e) trifluoromethyl, (f) benzlyloxy which may have on the phenyl nucleus such substitutents as halogens, alkoxy and phenoxy, (g) di(lower)alkylamino groups, and (h) phenyl, (3) cyclohexyl, (4) triphenylmethyl, (5) naphthylmethyl, (6) furylmethyl, (7) thiophenemethyl, (8) a lower alkyl substituted by a cycloalkyl of 5 to 13 carbon atoms, or (9) norbornene-2-methyl; and $R_{13}$ is (1) hydrogen, (2) benzyl, or (3) benzyl having on the phenyl nucleus one or more halogens or benzyloxy groups are substitutent]. These compounds are desirable because of their relatively low pulmonary toxicity. In the above formulas, lower alkyls include methyl, ethyl, and butyl; phenyl(lower)alkyls include benzyl, 2-phenylethyl, 1-phenylethyl, 3-phenylpropyl, 2,2-diphenylethyl, and dibenzylmethyl; phenyl(lower)alkyls having substituents on the phenyl nuclei include 2-p-chlorophenylethyl, p-chlorobenzyl, o-chlorobenzyl, m-chlorobenzyl, 1-(p-chlorophenyl)ethyl, o,p-dichlorobenzyl, m,p-dichlorobenzyl, p-bromobenzyl, p-fluorobenzyl, pentafluorobenzyl, m-trifluoromethylbenzyl, p-methylbenzyl, p-diethylaminobenzyl, p-methoxybenzyl, o,p-dimethoxybenzyl, m,p-dibenzyloxybenzyl, p-cyanobenzyl, and p-phenylbenzyl; and lower alkyls substituted by a cycloalkyl of 5 to 11 carbon atoms include cyclopentylmethyl, cyclohexylmethyl, cycloheptylmethyl, cyclooctylmethyl, cycloundecanylmethyl, and 2-cyclohexylethyl.

Especially desirable compounds are those represented by the general formula (I) in which R is 1-phenylethylaminopropylamino, butylaminopropylamino, or an amino group represented by the general formula (V)

$$-NH-(CH_2)_3-A_1-(CH_2)_3-B_1 \quad (V)$$

wherein $A_1$ is

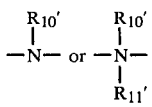

(where $R_{10}'$ and $R_{11}'$ are each a lower alkyl or benzyl) and $B_1$ is

[where $R_{12}'$ is (1) a phenyl(lower)alkyl which may have on the phenyl nuclues one or two substituents including (a) halogens, (b) cyano, and (c) benzyloxy group, or (2) a lower alkyl substituted by a cycloalkyl of 5 to 13 carbon atoms; and $R_{13}'$ is hydrogen or benzyl which may have one or two benzyloxy groups as substituents].

The combinations of X and R, which show an especially low pulmonary toxicity, are as follows:

(Amido)N-substituted bleomycins in which X is isopropyl, (S)-1-phenylethyl, diethylamino-1-methylbutyl, dibutylaminopropyl, or n-butylaminopropylamino and R is 1-phenylethylamino or N-(lower)alkyl-N-(halobenzylaminopropyl)aminopropylamino; salts thereof; (amido)N-substituted bleomycins in which X is an alkyl of 3 to 8 carbon atoms, 1,5-dimethylhexyl, benzyl, 1-phenylethylaminopropyl, di-n-butylaminopropyl, n-butylaminopropylaminopropyl, N-methyl-N-benzyl-N-(dibenzylaminopropyl)aminopropyl, or N-methyl-N-(halophenylethylaminopropyl)aminopropyl and R is N-methyl-N-(halophenylethylaminopropyl)aminopropylamino, N-methyl-N-benzyl-N-(dibenzylaminopropyl)aminopropylamino, N-methyl-N-[bis(m,p-dibenzyloxybenzyl)aminopropyl]aminopropylamino, N-methyl-N-methy-N-(dibenzylaminopropyl)aminopropylamino, N-ethyl-N-ethyl-N-(dibenzylaminopropyl)aminopropylamino, N-methyl-N-(cyclooctylmethylaminopropyl)aminopropylamino, or N-metyl-N-(cyanobenzylaminopropyl)aminopropylamino; and salts thereof.

As examples of the compounds of this invention, mention may be made of those shown in Table 1. In Table 1, "BLM" in the name of compound stands for "bleomycin" and the compound represented by the general formula (I) is designated as "name of R (amino residue)-(amido)N-[name of X]-BLM".

TABLE 1

| Compound No. | Name of compound | Abbreviation |
|---|---|---|
| 1 | 2-(4'-Imidazolyl)ethylamino-(amido)N—[methyl]-BLM | dH-MMA |
| 2 | 2-(4'-Imidazolyl)ethylamino-(amido)N—[ethyl]-BLM | dH-MEA |
| 3 | 2-(4'-Imidazolyl)ethylamino-(amido)N—[isopropyl]-BLM | dH-IPA |
| 4 | 2-(4'-Imidazolyl)ethylamino-(amido)N—[benzyl]-BLM | dH-BA |
| 5 | 2-(4'-Imidazolyl)ethylamino-(amido)N—[3-((S)-1'-phenylethyl)-aminopropyl]-BLM | dH-PEP |
| 6 | 2-(4'-Imidazolyl)ethylamino-(amido)N—[2-aminoethyl]-BLM | dH-EDA |
| 7 | 4-Guanidinobutylamino-(amido)N—[isopropyl]-BLM | dB2-IPA |
| 8 | 4-Guanidinobutylamino-(amido)N—[1',6'-dimethylheptyl]-BLM | dB2-DHA |
| 9 | 4-Guanidinobutylamino-(amido)N—[2',2',2'-trifluoroethyl]-BLM | dB2-TFEA |
| 10 | 4-Guanidinobutylamino-(amido)N—[octyl]-BLM | dB2-OCT |
| 11 | 4-Guanidinobutylamino-(amido)N—[3-((S)-1'-phenylethyl)amino- | dB2-PEP |

TABLE 1-continued

| Compound No. | Name of compound | Abbreviation |
|---|---|---|
| | propyl]-BLM | |
| 12 | 4-Guanidinobutylamino-(amido)N—[3-di-n-butylamino)propyl]-BLM | bB2-BPA |
| 13 | 4-Guanidinobutylamino-(amido)N—[lauryl]-BLM | dB2-LAA |
| 14 | 4-Guanidinobutylamino-(amido)N—[benzyl]-BLM | dB2-BA |
| 15 | 4-Guanidinobutylamino-(amido)N—[diphenylmethyl]-BLM | dB2-ADPM |
| 16 | 4-Guanidinobutylamino-(amido)N—[1',2'-diphenylethyl]-BLM | dB2-DPE |
| 17 | 4-Guanidinobutylamino-(amido)N—[β-naphthyl]-BLM | dB2-NA |
| 18 | 4-Guanidinobutylamino-(amido)N—[2-furylmethyl]-BLM | dB2-FFA |
| 19 | 4-Guanidinobutylamino-(amido)N—[3-pyridylmethyl]-BLM | dB2-AMPY |
| 20 | 4-Guanidinobutylamino-(amido)N—[2-thiazolylmethyl]-BLM | dB2-ATZ |
| 21 | 3-((S)-1'-phenylethyl)aminopropylamino-(amido)N—[isopropyl]-BLM | dPEP-IPA |
| 22 | 3-((S)-1'-phenylethyl)aminopropylamino-(amido)N—[3-((S)-1'-phenylethyl)aminopropyl]-BLM | dPEP-PEP |
| 23 | 3-((S)-1'-phenylethyl)aminopropylamino-(amido)N—[benzyl]-BLM | dPEP-BA |
| 24 | 3-((S)-1'-phenylethyl)aminopropylamino-(amido)N—[p-chlorobenzyl]-BLM | dPEP-CBA |
| 25 | 3-((S)-1'-phenylethylamino)propylamino-(amido)N—[stearyl]-BLM | dPEP-STE |
| 26 | 3-((S)-1'-phenylethylamino)propylamino-(amido)N—[lauryl]-BLM | dPEP-LAA |
| 27 | 3-((S)-1'-phenylethylamino)propylamino-(amido)N—[octyl]-BLM | dPEP-OCT |
| 28 | 3-((S)-1'-phenylethylamino)propylamino-(amido)N—[5-methyoxyindol-3-ylethyl]-BLM | dPEP-MTA |
| 29 | 3-((S)-1'-phenylethylamino)propylamino-(amido)N—[12-amimodo-decanyl]-BLM | dPEP-DAD |
| 30 | 3-((S)-1'-phenylethylamino)propylamino-(amido)N—[1',2'-diphenyl-ethyl]-BLM | dPEP-DPE |
| 31 | 3-((S)-1'-phenylethylamino)propylamino-(amido)N—[diphenylmethyl]-BLM | dPEP-ADPM |
| 32 | 3-((S)-1'-phenylethylamino)propylamino-(amido)N—[1,6-dimethyl-heptyl]-BLM | dPEP-DHA |
| 33 | 3-((S)-1'-phenylethylamino)propylamino-(amido)N—[2-(1-piperazinyl)ethyl]-BLM | dPEP-APZ |
| 34 | 3-((S)-1'-phenylethylamino)propylamino-(amido)N—[3-(di-n-butylamino)propyl]-BLM | dPEP-BPA |
| 35 | 3-((S)-1'-phenylethylamino)propylamino-(amido)N—[N—benzyl-piperazin-4-yl]-BLM | dPEP-ABP |
| 36 | 3-((S)-1'-phenylethylamino)propylamino-(amido)N—[4-diethylamino-1-methylbutyl]-BLM | dPEP-ADP |
| 37 | 3-[N—methyl-N—(3-n-butylaminopropyl)amino]propylamino-(amido)N—[isopropyl]-BLM | dBAPP-IPA |
| 38 | 3-[N—methyl-N—(3-n-butylaminopropyl)amino]propylamino-(amido)N—{3-[N—methyl-N—(3-n-butylaminopropyl)amino]-propyl}-BLM | dBAPP-BAPP |
| 39 | 3-{N—methyl-N—[3-(p-chlorobenzyl)aminopropyl]amino}-propylamino-(amino)N—[3-(S)-1'-phenylethyl)aminopropyl]-BLM | dMCLBZ-PEP |
| 40 | 3-{N—methyl-N—[3-(p-chlorobenzyl)aminopropyl]amino}-propylamino-(amido)N—[octyl]-BLM | dMCLBZ-OCT |
| 41 | 3-{N—methyl-N—[3-(p-chlorobenzyl)aminopropyl]amino}propyl-amino-(amido)N—[1,2-diphenylethyl]-BLM | dMCLBZ-DPE |
| 42 | 3-{N—methyl-N—[3-(p-chlorobenzyl)aminopropyl]amino}propyl-amino-(amido)N—[1,5-dimethylhexyl]-BLM | dMCLBZ-DHA |
| 43 | 3-{N—methyl-N—[3-(2-(p-chlorophenyl)ethyl)aminopropyl]amino}-propylamino-(amido)N—[3-((S)-1'-phenylethyl)aminopropyl]-BLM | dMCLPE-PEP |
| 44 | 3-{N—methyl-N—[3-(2-p-chlorobenzyl)ethyl)aminopropyl]amino}-propylamino-(amido)N—[octyl]-BLM | dMCLPE-OCT |
| 45 | 3-{N—methyl-N—[3-(2-(p-chlorophenyl)ethyl)aminopropyl]amino}-propylamino(amido)N—{3-[N—methyl-N—[3-(2-(p-chlorophenyl)-ethyl)aminopropyl]amino]propyl}-BLM | dMCLPE MCLPE |
| 46 | 3-{N—methyl-N—[3-(2-(p-chlorophenyl)ethyl)aminopropyl]amino}-propylamino-(amido)N—[3-(di-n-butylamino)propyl]-BLM | dMCLPE BPA |
| 47 | 3-{N—methyl-N—benzyl-N—[3-(dibenzylamino)propylamino}-propylamino-(amido)N—[3-((S)-1'-phenylethyl)aminopropyl]-BLM | dMTBZ-PEP |
| 48 | 3-{N—methyl-N—benzyl-N—[3-dibenzylamino)proplyamino}-propylamino-(amido)N—[octyl]-BLM | dMTBZ-OCT |
| 49 | 3-{N—methyl-N—benzyl-N—[3-(dibenzylamino)propylamino}-propylamino-(amido)N—{3-{N—methyl-N—benzyl-N—[3-dibenzyl-amino)propyl]amino}propyl}-BLM | dMTBZ-MTBZ |
| 50 | 3-{N—methyl-N—benzyl-N—[3-(dibenzylamino)propyl]amino}-propylamino-(amido)N—[3-[N—methyl-N—(3-n-butylaminopropyl)]-aminopropyl]-BLM | dMTBZ-BAPP |
| 51 | 3-{N—methyl-N—benzyl-N—[3-(dibenzylamino)propyl]amino}-propylamino-(amido)N—[benzyl]-BLM | dMTBZ-BA |
| 52 | 3-{N,N—dimethyl-N—[dibenzylamino)propyl]amino}-propylamino-(amido)N—[3-((S)-1'-phenyl)aminopropyl]-BLM | dMMDBZ-PEP |
| 53 | 3-{N,N—dimethyl-N—[3-(dibenzylamino)propyl]amino}-propylamino-(amido)N—[n-octyl]-BLM | dMMDBZ-OCT |
| 54 | 3-{N,N—dimethyl-N—[3-dibenzylamino)propyl]amino}-propylamino-(amido)N—[3-(di-n-butylamino)propyl]-BLM | dMMDBZ-BPA |
| 55 | 3-{N,N—diethyl-N—[3-(dibenzylamino)propyl]amino}-propyl-amino-(amido)N—[3-((S)-1'-phenylethyl)aminopropyl]-BLM | dEEDBZ-PEP |
| 56 | 3-{N,N—diethyl-N—[3-(dibenzylamino)propyl]amino}propylamino- | dEEDBZ- |

TABLE 1-continued

| Compound No. | Name of compound | Abbreviation |
|---|---|---|
|  | (amido)N—[octyl]-BLM | OCT |
| 57 | 3-{N,N—diethyl-N—[3-(dibenzylamino)propyl]amino}propylamino-(amido)N—[3-(di-n-butylamino)propyl]-BLM | dEEDBZ-BPA |
| 58 | 3-[N—methyl-N—[3-(cyclooctylmethylamino)propyl]amino}-propylamino-(amido)N—[3-(di-n-butyamino)propyl]-BLM | dMCO-BPA |
| 59 | 3-{N—methyl-N—[3-(cyclooctylmethylamino)propyl]amino}propyl-amino-(amido)N—[octyl]-BLM | dMCO-OCT |
| 60 | 3-{N—methyl-N—[3-(cyclooctylmethyl)aminopropyl]amino}-propylamino-(amido)N—[3-((S)-1'-phenylethylamino)propyl]-BLM | dMCO-PEP |
| 61 | 3-{N—methyl-N—[3-(p-cyanobenzylamino)propyl]amino}-propylamino-(amido)N—[3-(di-n-butylamino)propyl]-BLM | dMCNBZ-BPA |
| 62 | 3-{N—methyl-N—[3-(p-cyanobenzylamino)propyl]amino}propylamino-(amido)N—[octyl]-BLM | dMCNBZ-OCT |
| 63 | 3-{N—methyl-N—[3-(p-cyanobenzylamino)propyl]amino]propylamino-(amido)N—[(3-((S)-1'-phenylethylamino)propyl]-BLM | dMCNBZ-PEP |
| 64 | 3-{N—methyl-N—[3-bis(m,p-dibenzyloxybenzyl)aminopropyl]amino}-propylamino-(amido)N—[3-((S)-1'-phenylethyl)aminopropyl]-BLM | dMDDBZOBZ-PEP |
| 65 | 3-{N—methyl-N—[3-bis(m,p-dibenzyloxybenzyl)aminopropyl]amino}-propylamino-(amido)N—[n-octyl]-BLM | dMDDBZOBZ-OCT |

The present compounds represented by the general formula (I) are prepared as described below.

A compound represented by the following formula (VI) or reactive derivative of the carboxyl group thereof is allowed to condense with an amine (described later):

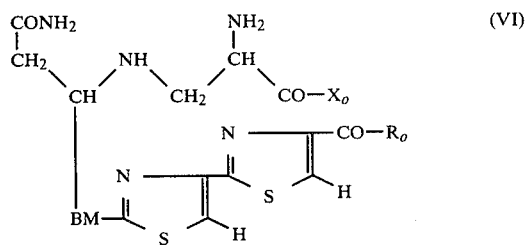

(VI)

wherein BM represents a moiety of bleomycin skeleton, $R_0$ represents a hydroxyl group or a terminal amino residue of bleomycins, $X_0$ represntes a hydroxyl group or a group of the formula —NH—X, at least either one of $R_0$ and $X_0$ being the hydroxyl group, and X represents (1) an alkyl of 1 to 18 carbon atoms, (2) an aminoalkyl of 1 to 12 carbon atoms, (3) a lower alkyl having as substituent (a) 1 to 3 halogen atoms, (b) 1 or 2 phenyl groups, (c) an indolyl group, or (d) a 5- or 6-membered heterocyclic group containing an oxygen, sulfur or nitrogen atom (among the substituent groups, the phenyl or indolyl group may be further substituted by a halogen atom or a lower alkoxy group), (4) $X_1$-lower alkyl [where $X_1$ is

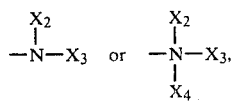

$X_2$ is a hydrogen atom, a lower alkyl or benzyl, $X_3$ is (a) a lower alkyl, (b) a phenyl(lower)alkyl, or (c) a moro- or di-(lower)alkylamino(lower)alkyl which may be substituted by a phenyl or halophenyl group, $X_4$ is (a) a lower alkyl or (b) a phenyl(lower)alkyl], (5) naphthyl, (6) thiazolyl, or (7) an N-phenyl(lower)alkylpiperazinyl. When $X_0$ in the formula (VI) is the hydroxyl group, an amine of the formula $$H_2N-X \quad (VII)$$

(wherein X is as defined above) is used in the condensation, while when $R_0$ in the formula (VI) is the hydroxyl group and $X_0$ is —NH—X (where X is as defined above), an amine of the formula $$H-R \quad (VIII)$$

(where R is as defined above) is used. If necessary, the condensation product is removed of the copper to obtain an (amido)N-substituted bleomycin of the general formula (I). Further, if necessary, a salt of the (amido)N-substituted bleomycin is prepared in a customary way.

The condensation of a compound of the formula (VI) or a reactive derivative of its carboxyl group with an amine of the formula (VII) or (VIII) is conducted according to the known procedure for forming an acidamide linkage, especially that used in peptide chemistry. A compound of the formula (VI) is allowed to react with an amine of the formula (VII) or (VIII) in the presence of those activation reagents for carboxyl group which are used in peptide chemistry. Alternatively, the compound of formula (I) is obtained by the reaction of an amine of the formula (VII) or (VIII) with a reactive derivative of the carboxyl group of a compound of formula (VI). The derivatives are, for example, a derivative obtained by reaction of an activation reagent for the carboxyl group and the compound of formula (VI) or a 3-aminopropyl ester of the carboxyl group of the compound of formula (VI). As examples of the activation reagents, mention may be made of 6-chloro-1-p-chlorobenzenesulfonyl-oxybenzotriazole, N-ethyl-5-phenylisooxazolium-3'-sulfonate, N-tert-butyl-5-methylisooxazolium perchlorate, N-ethoxycarbonyl-2-ethoxy-1,2-dihydroquinoline (FEDQ), di-p-nitrophenyl sulphite, tri-p-nitrophenyl phosphite, p-nitrophenyl trichloroacetate, dicyclohexylcarbodiimide (DCC), 1-ethyl-3-(3-dimethylaminopropyl)carbodiimide, 1-cyclohexyl-3-(2-morpholinoethyl)carbodiimide, diphenylcarbodiimide, di-p-tolylcarbodiimide, diisopropylcarbodiimide, diphenylphosphorazidate (DPPA), and diethyl phosphorocyanidate (DEPC).

As examples of the reactive derivatives of carboxyl group of the compounds of formula (VI), mention may be made of reactive derivatives obtained by the reaction of the above activation reagents with the carboxyl group; reactive derivatives of carboxyl group obtained by the joint use of the activation reagents and the condensation additives such as, for example, p-nitrophenol, o,p-dinitrophenol, pentachlorophenol, 2,4,5-trichlorophenol, pentafluorophenol, N-hydroxysuccinimide, 1-hydroxybenzotriazole, N-hydroxy-5-norbornene-2,3-dicarboximide; 3-aminopropyl ester of the carboxyl group of formula (VI), and monosubstituted 3-aminopropyl esters such as, for example, 3-acetylaminopropyl ester, 3-succinylaminopropyl ester, 3-benzoylaminopropyl ester, 3-benzylaminopropyl ester, 3-p-toluenesulfonylaminopropyl ester, 3-(2,4-dinitrophenyl)aminopropyl ester, 3-(3,5-dimethyl-3-oxocyclohexen-1-yl)aminopropyl ester, 3-(tert-butoxycarbonyl)aminopropyl ester, and 3-(salicylidene)iminopropyl ester.

The condensation is carried out generally in a solvent. The solvent may be any of those which will not affect the reaction, but it is preferred to use a polar solvent which dissolves the compound of formula (VI) used as a starting material. Examples of such solvents are water, dimethylformamide, dimethylacetamide, acetonitrile, and mixtures thereof. The molar ratio of the amine of formula (VII) or (VIII) to the compound of formula (VI) is generally about 0.5 to 20, preferably about 1 to 10. Although the reaction temperature depends upon the type of solvent and other conditions, yet it is generally $-15°$ to $45°$ C., preferably $-10°$ to $30°$ C. The reaction time is 1 to 70 hours. The process according to this invention is described below in detail.

The copper-containing form of the compound of formula (VI) and, if necessary, the above-noted additive are dissolved in water, dimethylformaldehyde, acetonitrile, or a mixture thereof. To the solution is added the above-noted activation reagent while stirring at $-5°$ to $15°$ C. If necessary, the mixture is adjusted to a pH suitable for activation with an inorganic acid or base such as hydrochloric acid or sodium hydroxide or with an organic base such as triethylamine or N-methylmorpholine. To the mixture is then added the amine component as such or in a solution of adjusted pH. The resulting mixture is stirred and, if necessary, pH is adjusted in a similar manner to that described above. The stirring is contained for 1 to 70 hours to yield the intended compound of this invention.

Isolation of the derivative thus formed is performed in the following manner. As organic solvent such as acetone or ether is added to the reaction mixture to precipitate the intended product. The precipitate is dissolved in distilled water, then adjusted to pH 6, and, for the purpose of desalting, is passed through a column packed with an adsorptive resin such as, for example, Amberlite ®XAD-2 (Rohm and Haas Co.) in distilled water to effect adsorption of the intended product to the resin. The column is washed with distilled water to remove the salt, and eluted with an acidified aqueous methanol such as a mixture of 1/50N hydrochloric acid and methanol (1:4 v/v) to collect the fractions having an absorption maximum at around a wave length of 290 m$\mu$. The combined fraction is neutralized with Dowex ®44 (an OH-type anion exchange resin of Dow Chemical Co.), then concentrated under reduced pressure, and lyophilized to obtain a crude powder of the derivative. In some cases, the desalting step may be omitted and the solution of the precipitate in distilled water can be directly subjected to the second step of treatment.

In the second step, the solution of crude powder in distilled water is passed through a column packed with CM-Sephadex ®C-25 (Na$^+$ type; Pharmacia Fine Chemicals Co.), which has been equalibrated with a 1/20M acetic acid-sodium acetate buffer solution (pH 4.5), to effect adsorption of the intended product. The adsorbed phase is then eluted by the linear concentration gradient technique which is carried out by continuously adding sodium chloride to the above buffer solution to increase the sodium chloride concentration gradually to 1.0M. In this step, the unreacted reactants and the by-products tend to be eluted in earlier stage and can be separated by means of an ultraviolet absorption monitor. If the fraction of the intended product is found to be contaminated with impurities, the chromatography is repeated to remove the entire impurities.

Alternatively, in place of the above chromatography, another method of chromatographic purification can be performed by employing an adsorptive resin Amberlite ®XAD-2 for example. The aqueous solution of the crude product is passed through the column packed with the resin in a buffer solution such as, for example, 1% aqueous ammonium acetate solution to effect adsorption of the intended product. The adsorbed phase is eluted by the linear concentration gradient technique in which methanol is continuously added to the buffer solution to increase gradually the methanol concentration. Since the unreacted reactants tend to be eluted in earlier stage and the main by-products in later stage, they can be separated by use of an ultraviolet monitor. If the intended fractions are found to be contaminated with impurities, they can be completely removed by repeating the chromatography.

The above two types of chromatography are performed each alone or in combination. The purified fraction containing the intended product is desalted by use of the adsorptive resin such as, for example, Amberlite ®XAD-2, and lyophilized to yield a blue amorphous powder of a copper-containing (amido)N-substituted bleomycin. The copper-free form is obtained by removing the copper from the copper-containing form by a known method such as the method employing EDTA as disclosed in Japanese Patent Publication No. 31,875/77. An example of the copper-removing procedure is described below.

The copper-containing product is dissolved in distilled water and the resulting solution is passes through a column packed with Amberlite ®XAD-2 in distilled water to effect adsorption of the copper-containing product. The resin is then washed with an aqueous solution containing sodium chloride and 5% of disodium salt of ethylenediaminetetraacetic acid (briefly EDTA.2Na) to carry away the copper ion by EDTA.2Na, leaving behind the copper-free (amino)N-substituted bleomycin adsorbed to the resin. The resin is then washed with a sodium chloride solution to remove EDTA.2Na, then with distilled water, and finally eluted with an acidified aqueous methanol such as, for example, a 1/50N aqueous hydrochloric acid-methanol (1:4 v/v) mixture to collect the fractions which show an absorption maximum at around 290 m$\mu$. The combined fraction is adjusted to pH 6.0 with Dowex ®44 (OH type; Dow Chemical Co.), concentrated under reduced pressure, and lyophilized to yield a white amorphous powder of a copper-free (amido)N-substituted bleomycin hydrochloride. If sodium sulfate and aqueous sulfuric acid are used in place of the sodium chloride and aqueous hydrochloric acid, there is obtained a sulfate. Thus, any desired salt can be obtained by selecting the salt and acid used in the elution step. As examples of salts obtained in such a manner, there may be listed acetate, tartarate, citrate, maleate and lactate in addition to the hydrochloride and sulfate.

When the (amido)N-substituted bleomycin prepared as described above is subjected to hydrolysis with 6N aqueous hydrochloric acid at 105° C. for 20 hours, there are detected, besides the amine R—H and X—NH$_2$ or a decomposition product of said amine in some cases, those decomposition products which are common to bleomycins, including L-threonine, β-amino-β-(4-amino-6-carboxy-5-methyl-pyrimidin-2-yl)propionic acid, 4-amino-3-hydroxy-2-methyl-n-pentanoic acid, β-hydroxy-L-histidine, β-amino-L-alanine, and 2'-(2-aminoethyl)-2,4'-bithiazole-4-carboxylic acid. This fact supports that the (amido)N-substituted bleomycin has the chemical structure represented by the aforementioned formula (I).

In the general formula (VI) of compounds used as starting material, when $X_0$ is a hydroxyl group and $R_0$ is a terminal amino residue of bleomycins, there is obtained a deamidobleomycin (copper-containing form) of the formula

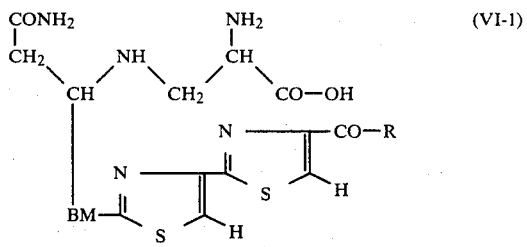

wherein BM and R are as defined previously. It is prepared by hydrolyzing copper-free bleomycins of the general formula (II) with an inactivating enzyme of rat or that similarly extracted from bovine or swine liver.

For instance, a bovine liver is homogenized in a phosphate buffer solution and centrifuged at 8,000 rpm. The supernatant is dialyzed against a phosphate buffer to obtain a crude enzyme solution. To this enzyme solution is added a solution of bleomycins in a phosphate buffer. The mixture is allowed to react at 37° C. for 5 to 48 hours and the reaction mixture is removed of the protein by suitable means [the protein can be removed, for example, by adding trichloroacetic acid (briefly TCA) to a concentration of 5% to precipitate the protein, separating the precipitate by centrifugation, and washing the precipitate three times with a 5% TCA solution to collect the washings]. The protein-free mixture is neutralized, mixed with copper acetate in excess to convert the intended product into a copper-chelate. For the purpose of desalting, the copper-chelate is passed through a column packed with an adsorptive resin, Dowex®HP 40, in distilled water to effect adsorption of the intended product. The salts are washed off with distilled water and the adsorbed phase is eluted with a 1/50N hydrochloric acid-methanol (1:4 v/v) mixture to collect fractions which show an absorption maximum at around 290 mµ. The collected fraction is neutralized with an anion exchange resin, Dowex®44 (OH type, Dow Chemical Co.), concentrated under reduced pressure, and lyophilized. The resulting powder is dissolved in distilled water and passed through a column packed with CM-Sephadex®C-25 (Na+ type; Pharmacia Fine Chemicals Co.) which has been equilibrated with a 1/20M acetic acid-sodium acetate buffer solution of pH 4.5 to effect adsorption. The adsorbed phase is eluted by the linear concentration gradient method in which sodium chloride is continuously added to the above buffer solution to increase gradually the sodium concentration to 1.0M. The eluate fractions, blue in color, containing the intended product are collected, desalted by the Diaion®HP 40 desalting method as described above, and lyophilized to yield a blue amorphous powder of copper-containing deamidobleomycins.

When $X_0$ is —NH—X (X is as defined previously) and $R_0$ is OH in the general formula (VI) of the compounds used as starting materials, the formula becomes that of an (amido)N-substituted bleomycinic acid;

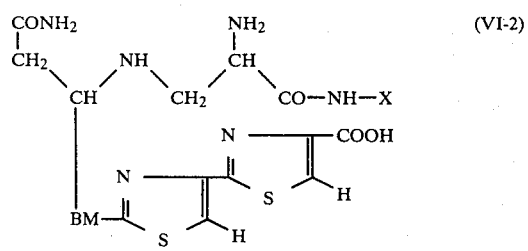

wherein BM is as defined previously. An example of the method of its synthesis is given below.

Using the above-mentioned inactivating enzyme, bleomycin B$_2$, a known compound, is converted into deamidobleomycin B$_2$, a deamidobleomycin of the formula (VI) in which $R_0$ is agmantine. This deamidobleomycin is allowed to react with an amine of the formula (VII) as described above to form an (amido)N-substituted bleomycin B$_2$ in which $R_0$ is agmantine, and hydrolyzing the resulting compound by use of a known fungal mycelium [for example, IFO 8502 deposited in Institute for Fermentation, Osaka] to yield the intended product.

Deamidobleomycinic acid represented by the formula

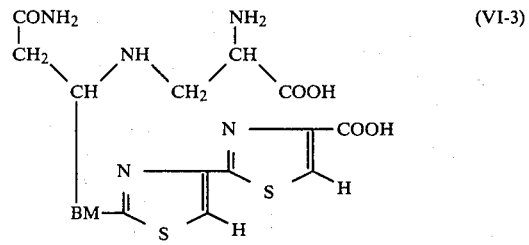

is a starting material of the general formula (VI) in which both $X_0$ and $R_0$ are hydroxyl groups. It is produced by hydrolyzing a known bleomycinic acid (see U.S. Pat. No. 3,886,133) with the aforementioned inactivating enzyme. It is also obtained by hydrolyzing deamidobleomycin B$_2$ of the general formula (VI-1), in which R is agmantine, by using the above-mentioned fungus cell.

As examples of the amines of general formula (VII), mention may be made of methylamine, ethylamine, n-propylamine, isopropylamine, n-butylamine, isobutylamine, tert-butylamine, n-penthylamine, 3-methylbutylamine, neopentylamine, n-heptylamine, 3-methylpentylamine, n-hexylamine, 1,5-dimethylhexylamine, isohexylamine, n-octylamine, n-decylamine, laurylamine, myristylamine, cetylamine, stearylamine, 2-aminoethylamine, 3-aminopropylamine, 4-aminobutylamine, 6-aminohexylamine, 12-aminododecylamine, 4-amino-4-methyl-1-dimethylpentylamine, 2,2,2-trifluoroethylamine, 2,2,2-trichloroethylamine, 2,2-difluoroethylamine, 2,2-dichloroethylamine, benzylamine, diphenylmethylamine, 2-phenylethylamine, 2,2-diphenylethylamine, 1-phenylethylamine, 1,2-diphenylethylamine, 3-phenylpropylamine, 2-phenylisopropylamine, 1,3-diphenylpropylamine, 3,3-diphenylpropylamine, 4-phenylbutylamine, 4,4-diphenylbutylamine, chlorobenzylamine, dichlorobenzylamine, bromobenzylamine, methoxybenzylamine, dimethoxybenzylamine, ethoxybenzylamine, methylenedioxybenzylamine, propoxybenzylamine, p-chlorophenylethylamine, p-methoxyphenylethylamine, p-benzyloxybenzylamine, furylmethylamine, 2-furylethylamine, 2-thiazolylmethylamine, 2-pyrazolylmethylamine, 2-imidazolylmethylamine, 4-imidazolylmethylamine, 2-thienylmethylamine, 2-pyridylmethylamine, 3-pyridylmethylamine, 4-pyridylmethylamine, indolylmethylamine, indolylethylamine, 4-methoxyindolylmethylamine, 2-pyrimidylmethylamine, 2-pyrimidylethylamine, 4-pyrimidylmethylamine, 4-pyrimidylethylamine, 2-piperidylmethylamine, 3-piperidylmethylamine, 4-piperidylmethylamine, 2-(2-piperidyl)ethylamine, 2-(3-piperidyl)ethylamine, 2-(4-piperidyl)ethylamine, 1-(2-piperidyl)ethylamine, 1-(3-piperidyl)ethylamine, 1-(4-piperidyl)ethylamine, 2-(piperidino)ethylamine, 2-piperazylmethylamine, 2-(2-piperazylethyl)amine, 2-(piperidino)ethylamine, 3-piperidinopropylamine, 2-(morpholino)ethylamine, 3-(morpholino)propylamine, 2-morpholinylmethylamine, 3-morpholinylmethylamine, 2-(morpholinyl)ethylamine, 3-(morpholinyl)propylamine, dimethylaminoethylamine, diethylaminoethylamine, dipropylaminoethylamine, propylaminoethylamine, dimethylaminopropylamine, diethylaminopropylamine, dipropylaminopropylamine, propylaminopropylamine, dibutylaminopropylamine, butylaminopropylamine, benzylaminopropylamine, 2-phenylethylaminopropylamine, 1-phenylethylaminopropylamine, 3-phenylpropylaminopropylamine, 4-phenylbutylaminopropylamine, methylaminoethylaminopropylamine, ethylaminopropylaminopropylamine, propylaminopropylaminopropylamine, butylaminopropylaminopropylamine, N-(butylaminopropyl)-N-methylaminopropylamine, dibutylaminopropylaminopropylamine, pentylaminopropylaminopropylamine, ethylaminobutylaminopropylamine, propylaminobutylaminopropylamine, ethylaminopropylaminobutylamine, butylaminopropylaminobutylamine, benzylaminoethylaminoethylamine, benzylaminoethylaminopropylamine, benzylaminopropylaminopropylamine, benzylaminobutylaminopropylamine, phenylethylaminopropylaminopropylamine, N-(phenylethylaminopropyl)-N-methylaminopropylamine, N-(chlorobenzylaminopropyl)-N-methylaminopropylamine, N-(bromobenzylaminopropyl)-N-methylaminopropylamine, N-(chlorophenylethylaminopropyl)-N-methylaminopropylamine, dibenzylaminopropyl-N,N-dimethylaminopropylamine, dibenzylaminopropyl-N,N-diethylaminopropylamine, dibenzylaminopropyl-N-methyl-N-benzylaminopropylamine, α-naphthylamine, β-naphthylamine, 2-thiazolylamine, 3-thiazolylamine, 4-thiazolylamine, N-benzyl-4-piperidylamine, N-phenylethyl-4-piperidylamine, N-benzyl-3-piperidylamine, and N-benzyl-2-piperidylamine.

Desirable amines of formula (VIII) are those aliphatic primary amines which have a basic group in addition to the amino group participating in the reaction. As examples of such amines, mention may be made of 2-aminoethylamine, 3-aminopropylamine, 2-dimethylaminoethylamine, 2-diethylaminoethylamine, 3-dimethylaminopropylamine, 3-diethylaminopropylamine, 3-(3-butylaminopropylamino)propylamine, 3-(2-hydroxypropylamino)propylamine, 3-piperidinopropylamine, 3-(1-phenylethylamino)propylamine, 2-aminopropylamine, 3-methylaminopropylamine, 3-butylaminopropylamine, 3-(6-aminohexylamino)propylamine, 3-trimethylaminopropylamine, 3-(3-dimethylaminopropylamino)propylamine, 3-(3-aminopropylamino)propylamine, 3-[N-methyl-N-(3-aminopropyl)amino]propylamine, 3-pyrrolidinylpropylamine, 3-piperidinylpropylamine, 3-morpholinopropylamine, 3-piperazinylpropylamine, 3-[4-(3-aminopropyl)piperazinyl]propylamine-3-(3-pyrrolidinylpropylamino)propylamine, 3-(3-piperidinylpropylamino)propylamine, 3-(3-morpholinylpropylamino)propylamine, 3-(3-hydroxypropylamino)propylamine, 3-(3-methoxypropylamino)propylamine, 3-benzylaminopropylamine, m-aminomethylbenzylamine, p-aminomethylbenzylamine, 2-cyclopentylaminoethylamine, 3-cyclohexylaminopropylamine, 4-cyclohexylaminobutylamine, cycloheptylaminopropylamine, 3-cyclooctylaminopropylamine, 3-[N-methyl-3-N-(cyclooctylmethylaminopropyl)amino]propylamine, 3-cyclodecanylmethylaminopropylamine, 3-{N-methyl-N-[3-(2-p-chlorophenylethylamino)propyl]amino}propylamine, 3-{N-methyl-N-[3-(m,p-dibenzyloxybenzyl)aminopropyl]amino}propylamine, 3-{N-methyl-N-[3-(p-cyanobenzylamino)propyl]amino}propylamine, 3-{N-methyl-N-[3-(cycloundecanylmethylamino)propyl]amino}propylamine, 3-{N-methyl-N-[bis(m,p-dibenzyloxybenzyl)aminopropyl]amino}propylamine, 3-{N,N-dimethyl-N-[3-(dibenzylamino)propyl]amino}propylamine, 3-{N,N-diethyl-N-[3-(dibenzylamino)propyl]amino}propylamine, 3-{N,N-dimethyl-N-[3-(N,N-dimethyl-N-(3-dibenzylaminopropyl)amino)propyl]amino}propylamine, 3-{N,N-dimethyl-N-[3-(N,N-dimethyl-N-(3-cyclooctylmethylaminopropyl)amino)propyl]amino} propylamine, 3-[4-(3-dibenzylaminopropylamino)piperidyl]propylamine, and 3-[4-(3-cyclooctylmethylaminopropyl)piperidyl]propylamine.

Among the amines of the general formula (VIII), those represented by the following general formula are novel compounds first synthesized by the present inventors:

$$NH_2-(CH_2)_3-A'-(CH_2)_3-B' \qquad (IX)$$

wherein A' represents

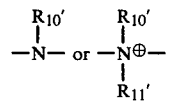

(where $R_{10}'$ and $R_{11}'$ are each a lower alkyl or benzyl and B' represents di[phenyl(lower)alkyl]amino, cyanophenyl(lower)alkylamino, $C_{5-13}$-cycloalkyl-substituted lower alkylamino, or bis[dibenzyloxyphenyl(lower)alkyl]amino. These compounds are synthesized by the hydrolysis of the compound represented by the general formula $$Y-(CH_2)_3-A'-(CH_2)_3-B' \quad (X)$$

(wherein A' and B' are as defined above and Y is a protected amino group) to remove the protective group. Although the hydrolysis takes place in the presence of either an acid or a base, yet an acid such as hydrochloric acid is generally preferred.

Of the starting materials of the general formula (X), those represented by the formula $$Y-(CH_2)_3-\overset{R_{10}'}{\underset{R_{11}'}{\overset{|}{N}}}\oplus-(CH_2)_3-\overset{R_{12}''}{\underset{R_{13}''}{\overset{|}{N}}} \quad (XI)$$

[wherein $R_{10}'$, $R_{11}'$ and Y are as defined above and $R_{12}''$ and $R_{13}''$ are each a phenyl(lower)alkyl] are prepared in the following manner.

A 3-aminopropyl-N,N-dialkylamine of the general formula $$NH_2-(CH_2)_3-\overset{R_{10}'}{\underset{R_{11}'}{\overset{|}{N}}} \quad (XII)$$

(wherein $R_{10}'$ and $R_{11}'$ are as defined above) is subjected to reductive condensation with benzaldehyde or a phenyl(lower)aldehyde. The reaction mixture is made alkaline and extracted with an organic solvent to obtain an N',N'-dibenzylaminopropyl-N,N-dialkylamine of the general formula $$R_{10}'-\overset{R_{11}'}{\overset{|}{N}}-(CH_2)_3-\overset{R_{12}''}{\overset{|}{N}}-R_{13}'' \quad (XIII)$$

(wherein $R_{10}'$, $R_{11}'$, $R_{12}''$ and $R_{13}''$ are as defined above). The resulting amine is allowed to react with a 3-halopropyl-N-(protected)amine to form a quaternary salt of the formula $$Y-(CH_2)_3-\overset{R_{10}'}{\underset{R_{11}'}{\overset{|}{N}}}\oplus-(CH_2)_3-\overset{R_{12}''}{\underset{R_{13}''}{\overset{|}{N}}} \quad (XIV)$$

wherein Y, $R_{10}'$, $R_{11}'$, $R_{12}''$ and $R_{13}''$ are as defined above. The quaternary salt is hydrolyzed in the presence of an acid, for example, 6N hydrochloric acid, at a temperature of from room temperature to 200° C., e.g. at 110° C. for 8 hours. After the removal of by-products such as an acid, the reaction mixture is concentrated to yield a hydrochloride of a compound of the formula (XI).

An amine of the general formula $$Y-(CH_2)_3-\overset{\text{lower alkyl}}{\overset{|}{N}}-(CH_2)_3-B'' \quad (XV)$$

wherein Y is as defined above and B'' is a di[phenyl(lower)alkyl]amino, p-cyanophenyl(lower)alkylamino, $C_{5-11}$-cycloalkyl-substituted lower alkylamino, or bis-[dibenzyloxyphenyl(lower)alkyl]amino, is prepared by acylating a bis(3-aminopropyl) (lower)alkylamine with one equivalent or less of an acylating agent such as, for example, benzoyl chloride, acetyl chloride, acetic anhydride, carbobenzoxy chloride, S-tert-butoxycarbonyl-4,6-dimethyl-2-mercaptopyrimidine, or N-carbethoxyphthalimide to form a monoacylated derivative, subjecting the resulting derivative to reductive condensation with one equivalent of an aldehyde when B'' is a monosubstituted amino group or with 2 or more, preferably 3 to 6, equivalents of an aldehyde when B'' is a disubstituted amino group, and hydrolyzing the acyl group with hydrochloric acid.

The physicochemical properties of the typical (amido)N-substituted bleomycin derivatives of this invention are as shown in Table 2.

TABLE 2

| Compound No. | Abbreviation | UV absorbtion maximum of Cu—free form, mμ (E 1%/1 cm) | TLC[*1] of Cu— containing form Rf | Electrophoresis[*2] of Cu—containing form, Rm (Rm of alanine = 1.0) |
|---|---|---|---|---|
| 1 | dH-MMA | 291 (111) | 0.62* | 0.92 |
| 2 | dH-MEA | 291 (107) | 0.75 | 0.83 |
| 3 | dH-IPA | 291 (105) | 0.56* | 0.85 |
| 4 | dH-BA | 291 (98) | 0.70 | 0.75 |
| 5 | dH-PEP | 291 (102) | 0.68 | 0.96 |
| 6 | dH-EDA | 291 (100) | 0.45 | 1.04 |
| 7 | dB2-IPA | 291 (89) | 0.53* | 0.93 |
| 8 | dB2-DHA | 291 (94) | 0.76 | 0.87 |
| 9 | dB2-TFEA | 291 (93) | 0.50* | 0.85 |
| 10 | dB2-OCT | 291 (85) | 0.72 | 0.77 |
| 11 | dB2-PEP | 291 (79) | 0.87 | 1.03 |
| 12 | dB2-BPA | 292 (79) | 0.87 | 1.02 |
| 13 | dB2-LAA | 291 (82) | 0.43 | 0.70 |
| 14 | dB2-BA | 291 (78) | 0.39* | 0.78 |
| 15 | dB2-ADPM | 291 (89) | 0.82 | 0.76 |
| 16 | dB2-DPE | 291 (81) | 0.77 | 0.76 |
| 17 | dB2-NA | 291 (85) | 0.84 | 0.83 |
| 18 | dB2-FFA | 292 (115) | 0.48* | 0.82 |
| 19 | dB2-AMPY | 292 (84) | 0.47* | 1.02 |
| 20 | dB2-ATZ | 292 (137) | 0.86 | 0.78 |
| 21 | dPEP-IPA | 291 (94) | 0.84 | 0.87 |
| 22 | dPEP-PEP | 291 (89) | 0.77 | 0.98 |
| 23 | dPEP-BA | 291 (91) | 0.78 | 0.87 |
| 24 | dPEP-CBA | 291 (81) | 0.74 | 0.79 |
| 25 | dPEP-STE | 291 (68) | 0.06 | 0.18 |
| 26 | dPEP-LAA | 291 (83) | 0.33 | 0.75 |
| 27 | dPEP-OCT | 291 (83) | 0.61 | 0.84 |

TABLE 2-continued

| Compound No. | Abbreviation | UV absorbtion maximum of Cu—free form, mμ (E 1%/1 cm) | TLC[*1] of Cu—containing form Rf | Electrophoresis[*2] of Cu—containing form, Rm (Rm of alanine = 1.0) |
|---|---|---|---|---|
| 28 | dPEP-MTA | 285 (100) | 0.75 | 0.81 |
| 29 | dPEP-DAD | 291 (94) | 0.78 | 1.02 |
| 30 | dPEP-DPE | 291 (88) | 0.65 | 0.87 |
| 31 | dPEP-ADPM | 291 (85) | 0.69 | 0.87 |
| 32 | dPEP-DHA | 291 (91) | 0.63 | 0.84 |
| 33 | dPEP-APZ | 291 (85) | 0.78 | 1.26 |
| 34 | dPEP-BPA | 291 (82) | 0.73 | 1.00 |
| 35 | dPEP-ABP | 291 (78) | 0.72 | 1.10 |
| 36 | dPEP-ADP | 291 (75) | 0.80 | 1.06 |
| 37 | dBAPP-IPA | 291 (91) | 0.85 | 1.14 |
| 38 | dBAPP-BAPP | 291 (83) | 0.26 | 1.44 |
| 39 | dMCLBZ-PEP | 289 (90) | 0.53 | 1.16 |
| 40 | dMCLBZ-OCT | 290 (88) | 0.50 | 1.08 |
| 41 | dMCLBZ-DPE | 290 (78) | 0.55 | 1.01 |
| 42 | dMCLBZ-DHA | 290 (80) | 0.53 | 0.90 |
| 43 | dMCLPE-PEP | 290 (79) | 0.53 | 1.04 |
| 44 | dMCLPE-OCT | 290 (85) | 0.52 | 0.96 |
| 45 | dMCLPE-MCLPE | 290 (79) | 0.25 | 1.20 |
| 46 | dMCLPE-BPA | 290 (83) | 0.60 | 1.11 |
| 47 | dMTBZ-PEP | 290 (81) | 0.38 | 1.06 |
| 48 | dMTBZ-OCT | 290 (73) | 0.24 | 0.92 |
| 49 | dMTBZ-MTBA | 290 (69) | 0.15 | 1.07 |
| 50 | dMTBZ-BAPP | 290 (71) | 0.47 | 0.79 |
| 51 | dMTBZ-BA | 290 (81) | 0.48 | 0.79 |
| 52 | dMMDBZ-PEP | 291 (75) | 0.50 | 1.15 |
| 53 | dMMDBZ-OCT | 291 (76) | 0.35 | 1.01 |
| 54 | dMMDBZ-BPA | 291 (79) | 0.49 | 1.13 |
| 55 | dEEDBZ-PEP | 291 (76) | 0.48 | 1.12 |
| 56 | dEEDBZ-OCT | 291 (78) | 0.33 | 1.00 |
| 57 | dEEDBZ-BPA | 291 (73) | 0.48 | 1.14 |
| 58 | dMCO-BPA | 291 (87) | 0.54 | 1.08 |
| 59 | dMCO-OCT | 291 (83) | 0.42 | 0.96 |
| 60 | dMCO-PEP | 291 (89) | 0.53 | 1.06 |
| 61 | dMCNBZ-BPA | 290 (81) | 0.70 | 1.10 |
| 62 | dMCNBZ-OCT | 292 (94) | 0.59 | 0.95 |
| 63 | dMCNBZ-PEP | 291 (93) | 0.69 | 1.10 |
| 64 | dMDDBZOBZ-PEP | 285 (74) | 0.09 | 0.93 |
| 65 | dMDDBZOBZ-OCT | 285 (76) | 0.04 | 0.64 |

Note:
[*1]"Silica Gel 60F 254 Silanised ®" (Merck Co.); methanol-6% ammonium acetate (60:40 v/v) except for Rf values with an asterisk which were measured in another mixture (65:34 v/v).
[*2]Avicel SF ® (FMC Co.); formic acid-acetic acid-water (27:75:900 v/v), 800 V, 15 minutes.

The biological properties, as determined on the typical compounds of this invention, are described below.

1. RESISTANCE TEST AGAINST INACTIVATING ENZYME (1) Extraction of inactivating enzyme.

The liver of Donryu strain male rats was mixed with two times the weight of a 1/15M phosphate buffer solution of pH 7 and ground to prepare a tissue emulsion. The resulting emulsion was centrifuged at 105,000 g (gravity constant) for 60 minutes. The supernatant was dialyzed and the resulting large molecule fraction was used as an inactivating-enzyme extract.

(2) Determination of inactivation reaction.

To 1 ml of the above extract, was added 1 ml of a substrate solutoin containing 800 mcg of a bleomycin derivative. The mixture was allowed to react at 37° C. for 40 minutes. A portion (0.3 ml) of the reaction mixture was removed of protein and tested for the residual activity against *Mycobacterium smegmatis* ATCC 607. Under the same conditions, bleomycin B2, used as control, showed 50% decrease in activity. The test results were as shown in Table 3. As is apparent from the test results, as compared with bleomycins, the (amido)N-substituted bleomycin derivatives of this invention are generally less affected by the bleomycin-inactivating enzyme.

2. ANTIMICROBIAL ACTIVITIES AGAINST *MYCOBACTERIUM SMEGMATIS* ATCC 607 AND *BACILLUS SUBTILIS*

The antimicrobial activity was tested against the captioned test organisms by the method of agar plate-cylinder. The activity was recorded on the assumption that the activity of standard sample of bleomycin $A_2$ (copper-free form) is 1,000 mcg poteney/mg. The test results were as shown in Table 3.

3. GROWTH INHIBITORY ACTIVITY AGAINST CULTURED HELA $S_3$ CELLS

HeLa $S_3$ cells were inoculated into a medium (MEM with 10% bovine serum) placed in a plastic petri dish. Two days thereafter, a bleomycin was added to the dish. After 3 days of breeding, the number of cells were counted. The percentage growth inhibition was calculated using the following equation:

Percentage inhibition $(\%) = 100 \times (B-A)/(B-C)$ where A is the final number of cells after 3 days from the addition of test sample, B is the final number of cells in the control without addition of the test smaple, and C is the number of cells at the time of addition of the test sample. $ID_{50}$ (concentration of 50% inhibition) was estimated from the graph prepared by plotting the concentration of test sample against the percentage inhibition. The results obtained were as shown in Table 3.

TABLE 3

| Compound No. | Abbreviation | Antimicrobial potency of Cu—free compound (mcg potency/mg) Against Mycobacterium smegmatis ATCC 607 | Against Bacillus subtilis | 50% Growth inhibitory concentration of Cu—free compd. against cultured HeLaS$_3$ cells (ID$_{50}$) mcg/ml | Resistance of Cu—free compound against inactivating enzyme*[1] |
|---|---|---|---|---|---|
| 1 | dH-MMA | 1447 | 654 | 1.2 | ++++ |
| 2 | dH-MEA | 1895 | 767 | 0.98 | +++ |
| 3 | dH-IPA | 2778 | 593 | 0.95 | +++++ |
| 4 | dH-BA | 6595 | 579 | 1.10 | + |
| 5 | dH-PEP | 9846 | 3772 | 1.0 | ++++ |
| 6 | dH-EDA | 2396 | 4453 | 1.0 | ++++ |
| 7 | dB2-IPA | 6425 | 1950 | 0.56 | ++++ |
| 8 | dB2-DHA | 24880 | 950 | 0.62 | +++ |
| 9 | dB2-TFEA | 3990 | 730 | 1.03 | ++ |
| 10 | dB2-OCT | 33700 | 1500 | 0.34 | + |
| 11 | dB2-PEP | 15729 | 7036 | 0.71 | +++++ |
| 12 | dB2-BPA | 16438 | 4384 | 0.98 | +++++ |
| 13 | dB2-LAA | 7650 | 660 | 0.39 | ++++ |
| 14 | dB2-BA | 28140 | 1650 | 0.73 | + |
| 15 | dB2-ADPM | 42320 | 980 | 0.39 | +++++ |
| 16 | dB2-DPE | 24480 | 520 | 0.67 | ++++ |
| 17 | dB2-NA | 33650 | 1295 | 1.1 | ± |
| 18 | dB2-FFA | 19150 | 1285 | 0.58 | ± |
| 19 | dB2-AMPY | 5160 | 1010 | 0.83 | ++ |
| 20 | dB2-ATZ | 4870 | 900 | 0.73 | ++ |
| 21 | dPEP-IPA | 11998 | 962 | 0.17 | ++++ |
| 22 | dPEP-PEP | 28030 | 2800 | 0.80 | +++++ |
| 23 | dPEP-BA | 38348 | 1380 | 0.26 | + |
| 24 | dPEP-CBA | 56328 | 1184 | 0.28 | + |
| 25 | dPEP-STE | 210 | 0 | 4 | * |
| 26 | dPEP-LAA | 3920 | 384 | 0.40 | ++++ |
| 27 | dPEP-OCT | 45100 | 886 | 0.36 | ++ |
| 28 | dPEP-MTA | 18650 | 586 | 0.60 | ++++ |
| 29 | dPEP-DAD | 14200 | 5400 | 0.43 | ++++ |
| 30 | dPEP-DPE | 33802 | 190 | 1.02 | ++++ |
| 31 | dPEP-ADPM | 54645 | 430 | 0.56 | +++++ |
| 32 | dPEP-DHA | 39956 | 298 | 0.83 | ++ |
| 33 | dPEP-APZ | 6359 | 5009 | 1.50 | ++++ |
| 34 | dPEP-BPA | 26023 | 2843 | 0.95 | ++++ |
| 35 | dPEP-ABP | 18537 | 2159 | 0.90 | ++++ |
| 36 | dPEP-ADP | 6061 | 3694 | 2.70 | ++++ |
| 37 | dBAPP-IPA | 13210 | 20048 | 0.90 | ++++ |
| 38 | dBAPP-BAPP | 5100 | 6600 | 0.79 | +++ |
| 39 | dMCLBZ-PEP | 14880 | 2590 | 0.53 | +++++ |
| 40 | dMCLBZ-OCT | 38200 | 1808 | 0.43 | +++ |
| 41 | dMCLBZ-DPE | 23342 | 521 | 0.86 | +++++ |
| 42 | dMCLBZ-DHA | 31834 | 933 | 0.49 | ++++ |
| 43 | dMCLPE-PEP | 15593 | 4267 | 0.37 | +++++ |
| 44 | dMCLPE-OCT | 38750 | 1898 | 0.23 | ++ |
| 45 | dMCLPE-MCLPE | 650 | 270 | 0.30 | +++++ |
| 46 | dMCLPE-BPA | 31690 | 3690 | 0.40 | +++++ |
| 47 | dMTBZ-PEP | 5900 | 180 | 2.15 | +++++ |
| 48 | dMTBZ-OCT | 2580 | 130 | 1.75 | * |
| 49 | dMTBZ-MTBZ | 230 | 1 | 11.0 | * |
| 50 | dMTBZ-BAPP | 1417 | 376 | 2.2 | ++++ |
| 51 | dMTBZ-BA | 24461 | 410 | 0.77 | +++ |
| 52 | dMMDBZ-PEP | 21371 | 2372 | 0.55 | +++++ |
| 53 | dMMDBZ-OCT | 40703 | 595 | 0.23 | * |
| 54 | dMMDBZ-BPA | 32633 | 2663 | 0.80 | ++++ |
| 55 | dEEDBZ-PEP | 20840 | 2150 | 1.00 | +++++ |
| 56 | dEEDBZ-OCT | 41380 | 520 | 0.60 | * |
| 57 | dEEDBZ-BPA | 25924 | 1831 | 1.5 | ++++ |
| 58 | dMCO-BPA | 62418 | 5518 | 0.40 | ++++ |
| 59 | dMCO-OCT | 65733 | 5473 | 0.23 | +++ |
| 60 | dMCO-PEP | 54345 | 7273 | 0.33 | +++++ |
| 61 | dMCNBZ-BPA | 14730 | 4755 | 1.10 | ++++ |
| 62 | dMCNBZ-OCT | 49270 | 381 | 0.28 | +++ |
| 63 | dMCNBZ-PEP | 21877 | 11056 | 0.60 | ++++ |
| 64 | dMDDBZOBZ-PEP | 115 | 23 | 0.058 | * |
| 65 | dMDDBZOBZ-OCT | 153 | 13 | 0.30 | * |

Note:
*[1] The resistance was rated in terms of the degree of inactivation under the conditions under which the degree of inactivation of bleomycin B$_2$ is 50%.

| Rating | Degree of inactivation |
|---|---|
| ± | 45% or more |
| + | 35 to 44% |
| ++ | 25 to 34% |
| +++ | 15 to 24% |
| ++++ | 5 to 14% |

TABLE 3-continued

+++++ less than 5%
\* Undeterminable because of the adsorption to the enzyme protein.

4. PULMONARY TOXICITY (PULMONARY FIBROSIS) IN MICE

ICR strain mice (male, 15 weeks old) in groups of 9 members were used. Each test preparation was administered by intraperitoneal injection once a day for 10 consecutive days at a dose rate of 5 mg/kg. After completion of the administration, the mice were bred for 5 weeks under observation, then slughtered and autopsied to examine the incidence and grade of the pulmonary fibrosis. The evaluation was made by comparing the number of administered mice suffering from pulmonary fibrosis and the grade of the disease. The results were as shown in Table 4. The grade was numerically rated as follows:

Number of points

0: No fibrosis.
1: Accumulation of exudate in alveolus and fibrosis-like change in alveolar septum.
2: Fibrosis in several areas.
4: Scattered fibrosis.
6: Fibrosis in more than two-thirds of the total area.

The "ratio" in Table 4 was calculated by comparison with "Bleomycin Complex."

TABLE 4

| Compound No. | Abbreviation | Incidence Number of mice with pulmonary fibrosis (%) | | Grade Total score of pulmonary fibrosis/ total number of samples (%) | | Ratio |
|---|---|---|---|---|---|---|
| 21 | dPEP-IPA | 3/8 | (38) | 5/24 | (21) | 0.27 |
| 22 | dPEP-PEP | 1/8 | (13) | 1/21 | (4) | 0.05 |
| 33 | dPEP-APZ | 5/9 | (56) | 11/27 | (41) | 0.44 |
| 34 | dPEP-BPA | 0/8 | (0) | 0/24 | (0) | 0 |
| 37 | dBAPP-IPA | 3/9 | (33) | 13/27 | (48) | 0.46 |
| 38 | dBAPP-BAPP | 5/7 | (71) | 7/21 | (33) | 0.32 |
| 39 | dMCLBZ-PEP | 2/9 | (20) | 2/27 | (7) | 0.07 |
| 43 | dMCLPE-PEP | 0/1 | (0) | 0/3 | (0) | 0 |
| 45 | dMCLPE-MCLPE | 0/9 | (0) | 0/27 | (0) | 0 |
| 47 | dMTBZ-PEP | 0/8 | (0) | 0/24 | (0) | 0 |
| 48 | dMTBZ-OCT | 0/8 | (0) | 0/24 | (0) | 0 |
| 49 | dMTBZ-MTBZ | 0/3 | (0) | 0/9 | (0) | 0 |
| 51 | dMTBZ-BA | 0/8 | (0) | 0/24 | (0) | 0 |
| 52 | dMMDBZ-PEP | 0/9 | (0) | 0/27 | (0) | 0 |
| 53 | dMMDBZ-OCT | 0/9 | (0) | 0/27 | (0) | 0 |
| 54 | dMMDBZ-BPA | 0/9 | (0) | 0/27 | (0) | 0 |
| 55 | dEEDBZ-PEP | 0/9 | (0) | 0/27 | (0) | 0 |
| 56 | dEEDBZ-OCT | 0/9 | (0) | 0/27 | (0) | 0 |
| 57 | dEEDBZ-BPA | 0/9 | (0) | 0/27 | (0) | 0 |
| 58 | dMCO-BPA | 0/9 | (0) | 0/27 | (0) | 0 |
| 59 | dMCO-OCT | 0/9 | (0) | 0/27 | (0) | 0 |
| 60 | dMCO-PEP | 0/9 | (0) | 0/27 | (0) | 0 |
| 62 | dMCNBZ-OCT | 0/9 | (0) | 0/27 | (0) | 0 |
| 64 | dMDDBZOBZ-PEP | 0/9 | (0) | 0/27 | (0) | 0 |
| 65 | dMDDBZOBZ-OCT | 0/9 | (0) | 0/27 | (0) | 0 |

5. $LD_{50}$ IN MICE, AS DETERMINED BY ADMINISTRATION FOR 10 CONSECUTIVE DAYS $CDF_1$/SLC strain male mice (6 weeks old, 7 members per group) were subcutaneously administered with various doses of bleomycin derivatives once a day for 10 consecutive days. From the mortality during the administration period, $LD_{50}$ (daily dose) was determined by the method of Behrens-Kärber. The results were as shown in Table 5.

TABLE 5

| Compound No. | Abbreviation | $LD_{50}$ during administration period of 10 consecutive days. (mg/kg/day) |
|---|---|---|
| 52 | dMMDBZ-PEP | 13.9 |
| 53 | dMMDBZ-OCT | 15.0 |
| 64 | dMDDBZOBZ-PEP | >81.4 |
| 65 | dMDDBZOBZ-OCT | >75.7 |

As is apparent from the foregoing description, the compounds of the present invention are resistant to a beomycin-inactivating enzyme, have a high growth-inhibitory activity against cultured HeLa $S_3$ cells as well as a distingished antimicrobial activity, and are very low in pulmonary toxicity, positively suggesting their usefulness in clinical fields.

When used as a drug, the compounds of this invention are mixed with an excipient in a customary way and prepared in the form of injections, tablets, ointments, suppositories, and so on. Suitable excipients include water, sugars such as mannitol, and other materials usually used in medical preparations.

Although the dose varies depending on the administration form, a single dose of 2–10 mg per person is administered one to four times a week, the cumulative dose being 2–200 mg/person/week.

The invention is illustrated below in detail with reference to Examples, but the invention is not limited thereto.

EXAMPLE 1

Step A

Fresh bovine liver, 200 g in weight, was homogenized in 400 ml of a 0.05M phosphate buffer solution of pH 7.2 and centrifuged at 8,000 rpm for 30 minutes. The supernatant was dialyzed against 0.05M phosphate buffer to prepare a crude enzyme solution. To 10 g of bleomycin $B_2$, was added 400 ml of the crude enzyme solution. The mixture was allowed to react at 37° C. for 24 hours. To the reaction mixture, was added 40 ml of a 55% solution of trichloroacetic acid (briefly TCA) to precipitate the protein. The precipitate was separated by centrifuging and washed three times with 5% TCA solution. The supernatant and the washings were combined, neutralized with a 4M sodium hydroxide solution, and admixed with 3.2 g (2.4 equivalents to bleomycin) of copper acetate to form a copper-chelate of the intended product. For the purpose of desalting, the copper-chelate solution was passed through a column, 1 liter in volume, packed with an adsorptive resin Diaion ®HP 40 (Mitsubishi Chemical Co.) in distilled water, to effect the adsorption of intended product. After washing off the salts with 1.5 liters of distilled water, the adsorbed phase was eluted with a 1/50N aqueous hydrochloric acid-methanol (1:4 v/v) mixture to collect the fractions which show an absorption maximum at around a wave length of 290 m$\mu$. The combined fraction was neutralized with Dowex ®44 (OH type, Dow chemical Co.) and concentrated under reduced pressure. The concentrate was passed through a column, 1 liter in volume, packed with CM-Sephadex ®C-25 (Na$^+$ type, Pharmacia Fine Chemicals Co.), which had been equilibrated with a 1/20M acetic acid-sodium acetate buffer solution of pH 4.5, to effect adsorption. The adsorbed phase was eluted by the linear concentration gradient method in which sodium chloride was continuously added to the above-noted buffer solution to increase gradually the sodium concentration to 1.0M. The blue fractions eluted at a sodium concentration of about 0.3M were collected, then desalted by using Diaion ®HP 40 as described above, and lyophilized to yield 8.5 g (83% yield) of a blue amorphous powder of copper-containing deamidobleomycin $B_2$.

The blue powder showed absorption maxima (E 1%/1 cm) at 242 m$\mu$ (138) and 291 m$\mu$ (115), as determined in distilled water. The infrared absorption maxima (in wave number, cm$^{-1}$), as measured in KBr-tablet, were 3425, 2975, 2940, 1720, 1640, 1575, 1460, 1420, 1400, 1375, 1280, 1260, 1240, 1190, 1140, 1100, 1060, 1020, 760. Other physicochemical properties were as shown in Table 6.

In a similar manner to that described above, by using belomycin $A_2'$-C, 3-((S)-1'-phenylethyl)aminopropylaminobleomycin, and 3-(3-n-butylaminopropylamino)propylaminobleomycin, there were obtained deamidobleomycin $A_2'$-C, 3-((S)-1'-phenylethylamino)propylamino-deamidobleomycin, and 3-(3-n-butylaminopropylamino)propylaminodeamidobleomycin, respectively. The physicochemical properties of these compounds were as shown in Table 6.

TABLE 6

| Synthesized deamidobleomycin | UV absorption maximum of Cu— containing form m$\mu$ (E 1%/1cm) | | TLC*[1] of Cu— containing form, Rf | Electrophoresis*[2] of Cu—containing form, Rm (Rm of alanine = 1.0) |
|---|---|---|---|---|
| Deamidobleomycin $B_2$ | 242 | (138) | 0.95 | 0.72 |
|  | 292 | (115) | 0.64* |  |
| Deamidobleomycin $A_2'$-C | 242 | (132) | 0.75 | 0.62 |
|  | 292 | (110) | 0.46* |  |
| 3-((S)—1'-phenylethylamino)propyl-deamidobleomycin | 242 | (147) | 0.87 | 0.67 |
|  | 292 | (124) | 0.40* |  |
| 3-(3-n-butylaminopropylamino)propylamino-deamidobleomycin | 242 | (142) | 0.83 | 1.01 |
|  | 292 | (118) | 0.55* |  |

Note:
*[1]"Silica Gel 60F 254 Silanised ®" (Merck Co.); measured in methanol-6% ammonium acetate solution mixture (60:40 v/v) except for Rf values with an asterisk which were measured in another mixture (65:34 v/v)
*[2]Avicel SF ® (FMC Co.); formic acid-acetic acid-water (27:75:900v/v); 800 V, 15 minutes.

Step B

To a solution of 1 g of copper-containing deamidobleomycin $B_2$ obtained in step A and 1.77 g of 1-hydroxybenzotriazole (briefly HOBT) in 10 ml of dimethylformamide, while being cooled at 0° C. and stirred, was added 1.35 g (10 equivalents to bleomycin) of dicyclohexylcarbodiimide (briefly DCC). Five minutes thereafter, to the mixture were added 840 mg (5 equivalents to bleomycin) of 3-((S)-1'-phenylethylamino)propylamine hydrochloride and 0.72 ml of N-methylamorpholine. The resulting mixture was allowed to react with stirring at room temperature for 16 hours. To the reaction mixture was added 10 times by volume of acetone to precipitate the intended product. After thorough washing with acetone, the precipitate was dissolved in distilled water and passed through a column, 100 ml in volume, packed with CM-Sephadex ®C-25 (Na$^+$ type, Pharmacia Fine Chemicals Co.), which had been equilibrated with a 1/20M acetic acid-sodium acetate buffer solution of pH 4.5, to effect adsorption. The adsorbed phase was eluted by the linear concentration gradient method in which sodium chloride was continuously added to the above-noted buffer solution to increase gradually the sodium concentration to 1.0M. The blue fractions eluted at a sodium concentration of around 0.6M were collected. The combined fraction was desalted by using 100 ml of Diaion ®HP-40 as described above, and lyophilized to yield 880 mg (76% yield) of a blue amorphous powder of copper-containing amido(N)-[3-((S)-1'-phenylethylamino)propyl]-bleomycin $B_2$. It showed absorption maxima (E 1%/1 cm) at 243 m$\mu$ (125) and 292 m$\mu$ (96), as measured in distilled water. The IR absorption (in wave number, cm$^{-1}$), as measured in KBr-table, were 3425, 2975, 2930, 1720, 1640, 1580, 1575, 1550, 1455, 1430, 1400, 1370, 1290, 1240, 1190, 1130, 1095, 1060, 1005, 980, 875, 760. Other physicochemical properties were as shown in Table 2.

In a similar manner to that described above, copper-containing forms of (amido)N-substituted bleomycin $B_2$ Nos. 7 to 20 shown in Table 2 were synthesized by the reaction of copper-containing deamidobleomycin $B_2$ with amines corresponding to the intended products.

Similarly, compound Nos. 1, 6, 21-38, 64 and 65 shown in Table 2 were synthesized by the reaction of deamidobleomycin $A_2'$-C, 3-((S)-1'-phenylethyl)amino-propylamino-deamindobleomycin, and 3-(3-n-butylaminopropylamino)propylamino-deamidobleomycin (each deamidobleomycin in copper-containing form) with amines corresponding to the intended products.

Step C

Into 20 ml of distilled water, was dissolved 880 mg of the copper-containing compound obtained in step B. For the purpose of desalting, the solution was passed through a column, 100 ml in volume, packed with Amberlite ®XAD-2 in distilled water, to effect adsorption of the copper-containing compound. The resin was washed successively with 300 ml of an aqueous solution containing sodium chloride and 5% of EDTA.2Na, 100 ml of 2% aqueous sodium chloride solution, and 250 ml of distilled water. The resin was then eluted with a 1/50N hydrochloric acid-methanol (1:4 v/v) mixture to collect the fractions which show an absorption maximum at a wave length of around 290 m$\mu$. The combined fraction was adjusted to pH 6.0 with Dowex 44 (OH type, Dow Chemical Co.), then concentrated under reduced pressure, and lyophilized to yield 790 mg (93% yield) of a white amorphous powder of copper-freee (amido)N-[3-((S)-1'-phenylethylamino)propyl]-bleomycin $B_2$ hydrochloride. UV absorption maximum and (E 1%/1 cm) were 291 m$\mu$ and (79), respectively. IR absorption maxima (in wave number, cm$^{-1}$), as measured in KBr-tablet were 3425, 2950, 1720, 1640, 1555, 1450, 1400, 1360, 1320, 1260, 1190, 1060, 880, 910, 805, 770, and 700. Other physicochemical properties were as shown in Table 2.

EXAMPLE 2

Step A

Fungal mycelium, 400 g in weight, obtained by cultivating *Fusarium roseum* IFO 7189 deposited in the Institute for Fermentation, Osaka, was homogenized in 4 limiters of a 1/20M phosphate buffer solution of pH 7.5. To the homogenized mixture, was added a solution of 10 g of copper-containing (amido)N-[3-((S)-1'-phenylethylamino)propyl]-bleomycin $B_2$ in 1 liter of the same phosphate buffer solution as used above. The mixture was allowed to react at 37° C. for 20 hours. The reaction mixture was mixed with a filter aid and suction-filtered. The residue was washed with the same buffer solution as used above. The filtrate and washings were combined and passed through a column packed with 1 liter of an adsorptive resin Amberlite ®XAD-2 in distilled water, to effect adsorption of the intended product. After washing off the salts with 2 liters of distilled water, the adsorbed phase was eluted with 50% aqueous methanol to collect 5 liters of blue or bluish green fractions. The combined fraction was concentrated under reduced pressure, then dissolved in 350 ml of 80-% methanol, and passed through a column packed with 70 ml of alumina in 80-% methanol. The column was washed with 100 ml of 80-% methanol, and developed with 40-% methanol to collect 350 ml of the blue eluate fractions. The combined fraction was concentrated under reduced pressure, then dissolved in distilled water, and passed through a column, 600 ml in volume, packed with CM-Sephadex ®C-25 (Na$^+$ type, Pharmacia Fine Chemicals Co.) which had been equilibrated with a 1/20M acetic acid-sodium acetate buffer solution of pH 4.5, to effect adsorption of the intended product. The adsorbed phase was eluted by the linear concentration gradient method in which sodium chloride was continuously added to the above buffer solution to increase gradually the sodium concentration to 1.0M. The blue fractions eluted at a sodium concentration of around 0.2M were collected, then desalted by use of Diaion ®HP 40, and lyophilized to yield 7.1 g (79% yield) of a blue amorphous powder of copper-containing (amido)N-[3-((S)-1'-phenylethylamino)-propyl]-bleomycinic acid. UV absorption maxima and (E 1%/1 cm) measured in distilled water were 245 m$\mu$ (121) and 293 m$\mu$ (119), respectively. IR absorption maxima (in wave number, cm$^{-1}$), as mesured in KBr-tablet were 3450, 2975, 2940, 1720, 1645, 1580, 1555, 1460, 1370, 1300, 1190, 1140, 1095, 1060, 1005, 980, 880, 765, and 700. Other physicochemical properties were as shown in Table 7.

In a similar manner to that described above, (amido)N-n-octyl-bleomycinic acid and (amido)N-(3-dibutylaminopropyl)-bleomycinic acid were obtained from (amido)N-n-octylbleomycin $B_2$ and (amido)N-(3-dibutylaminopropyl)bleomycin $B_2$, respectively. The physicochemical properties of these acids were as shown in Table 7.

TABLE 7

| Synthesized (amido)N—substituted bleomycinic acid | UV absorption maximum of Cu—containing form, m$\mu$ (E 1%/1 cm) | TLC[*1] of Cu—containing form, Rf | Electrophoresis[*2] of Cu—containing form, Rm (Rm of alanine = 1.0) |
|---|---|---|---|
| (Amido)N—[3-((S)-1'-phenylethylamino)-propyl]bleomycinic acid | 245 (121) 293 (119) | 0.93 0.62* | 0.84 |
| (Amido)N—(3-dibutylaminopropyl)bleomycinic acid | 247 (123) 294 (123) | 0.93 0.62* | 0.88 |
| (Amido)N—(octyl)bleomycinic acid | 245 (130) 293 (128) | 0.79 0.20* | 0.59 |

Note:
[*1]"Silica Gel 60F 254 Silanised ®" (Merck Co.); measured in methanol-6% ammonium acetate solution mixture (60:40 v/v) except for Rf values with an asterisk which were measured in another mixture (65:34 v/v).
[*2]Avicel SF ® (FMC CO.); formic acid-acetic acid-water (27:75:900 v/v); 800 V, 15 minutes.

Step B

Into 10 ml of DMF, were dissolved 1.0 g of Cu-containing (amido)N-[3-((S)-1'-phenylethylamino)propyl]-bleomycinic acid prepared in step A and 1.71 g of HOBT. In a manner similar to that in step B of Example 1, using 1.31 g of DCC, the above solution was allowed to react with 340 mg of 3-[N-(3'-cyclooctylmethylamino)propyl-N-methylamino]propylamine for 3 hours to form a condensation product. As in Example 1, the reaction mixture was treated with acetone, then purified by the CM-Sephadex ® chromatography, and passed through a column of 100 ml of Amberlite ®X-AD-2 to effect adsorption. The adsorbed phase was eluted by the linear concentration gradient method in which 500 ml of methanol was continuously added to 500 ml of an acetate buffer solution of pH 4.5 to increase linearly the methanol concentration. The intended product was eluted at a methanol concentration of 40 to 50%. The eluate was desalted by using a column (100 ml) of Diaion ®HP 40, as described above, and lyophilized to yield 980 mg (83% yield) of a blue amorphous powder of 3-[N-3'-(cyclooctylamino)propyl-N-methylamino]propylamino-(amido)N-[3-((S)-1'-phenylethylamino)propyl]-bleomycin (copper-containing form).

Step C

Into 22 ml of distilled water, was dissolved 980 mg of copper-containing 3-[N-(3'-cyclooctylmethylamino)-propyl-N-methylamino]propylamino-(amido)N-[3-((S)-1'-phenylethyl)aminopropyl]-bleomycin prepared in step B. The solution was subjected to the copper removal treatment, as in Example 1, by using Amberlite ®XAD-2 and a 5% aqueous EDTA.2Na solution. The effluent from the column was lyophilized to yield 870 mg (92% yield) of a colorless amorphous powder of copper-free 3-[N-(3'-cyclooctylmethylamino)propyl-N-methylamino]propylamino(amido)N-[3-((S)-1'-phenylethylamino)propyl]-bleomycin hydrochloride. UV absorption maximum and (E 1%/1 cm) as measured in distilled water were 291 m$\mu$ and (89), respectively. IR absorption maxima (in wave number, cm$^{-1}$) as measured in KBr-tablet were 3400, 2925, 1720, 1650, 1550, 1520, 1480, 1460, 1450, 1405, 1385, 1360, 1320, 1255, 1190, 1130, 1100, 1055, 1020, 980, 960, 880, 805, 760, 725, and 695. Other physicohcemical properties were as shown in Table 2.

In a similar manner to that described above, copper-free forms of the compounds No. 20 to No. 63 shown in Table 2 were obtained from the corresponding starting materials.

EXAMPLE 3

Step A

In a manner similar to that described in Example 2, 1.5 g of the copper-containing deamidobleomycin B$_2$ prepared in Example 1 was mixed with a homogenised mixture of 60 g of cultured mycelium of *Fusarium roseum* and 750 ml of a 1/20M phosphate buffer solution of pH 7.5. The mixture was allowed to react at 37° C. for 21 hours. The reaction mixture was treated as in Example 2 and passed through a column (500 ml in volume) of Amberlite XAD ®-2 to effect adsorption of the intended substance. The column was washed with 750 ml of distilled water, and eluted with a water-methanol (4:1) mixture to collect green fractions (750 ml in total) which were concentrated under reduced pressure. The concentrate was passed through a column, 60 ml in volume, packed with CM-Sephadex ® C-25 (Na+ type, Pharmacia Fine Chemicals Co.) which had been equilibrated with a 1/20M acetic acid-sodium acetate buffer solution of pH 4.5. The column was washed with distilled water and the effluent blue fractions (80 ml in total) were collected. After repeating the CM-Sephadex ® chromatography, the purified blue fraction was concentrated, and passed through a column, 1 liter in volume, packed with Sephadex ®LH-20 (Pharmacia Fine Chemicals Co.) in a water-methanol (1:4) mixture. The column was developed with a water-methanol (1:4) mixture to collect blue fractions. The combined blue fraction was concentrated under reduced pressure and lyophilized to yield 890 mg (87% yield) of a blue amorphous powder of copper-containing deamidobleomycinic acid. UV absorption maximum and (E 1%/1 cm) as measured in distilled water were 254 m$\mu$ (143), and 292 m$\mu$ (144), respectively. IR absorption maxima (in wave number, cm$^{-1}$) as measured in KBr-table were 3450, 2975, 2940, 1720, 1640, 1560, 1465, 1420, 1380, 1280, 1190, 1140, 1100, 1060, 1020, 990, 880, 810, and 775. Under the conditions shown in Table 7, Rf value in thin layer chromatography was 0.91* and Rm value in electrophoresis was 0.49.

Step B

Into 5 ml of dimethylformamide, were dissolved 500 mg of the coper-containing compound obtained in step A and 2,010 mg of HOBT. The resulting solution and 3-((S)-1'-phenylethylamino)propylamine were subjected to condensation for 21 hours, as in Example 1, using 770 mg of DCC. Similarly to Example 2, the reaction mixture was treated with acetone, purified by CM-Sephadex ® chromatography and Amberlite ®X-AD-2 chromatography, desalted by use of Diaion ®HP-40, and lyophilized to yield 280 mg (42% yield) of a blue amorphous powder of copper-containing 3-((S)-1'-phenylethylamino)propylamino-(amido)N-[3-((S)-1'-phenylethylamino)propyl]-bleomycin.

In a manner similar to that described above, 3-(3-n-butylaminopropylamino)propylamino-(amido)N-[3-(3-n-butylaminopropylamino)propyl]-bleomycin and 3-{N-3-[2-(p-chlorophenyl)ethylamino]propyl-N-methylamino}propylamino-(amido)N-[3-(2-(p-chlorophenyl)ethylamino)propyl-N-methylaminopropyl]-bleomycin were obtained by using 3-(3-n-butylaminopropylamino)propylamine and N-[N-(3-aminopropyl)-N-methylaminopropyl]-N-[2-(p-chlorophenyl)ethyl]amine, respectively.

Step C

Into 8 ml of distilled water, was dissolved 280 mg of the copper-containing 3-((S)-1'-phenylethylamino)-propylamino-(amido)N-[3-((S)-1'-phenylethyl)aminopropyl]-bleomycin obtained in step B. The solution was subjected to the copper-removing treatment as in Example 1 using Amberlite ®XAD-2 and 5-% aqueous EDTA.2Na solution. The effluent from the column was lyophilized to yield 250 mg (92% yield) of a white amorphous powder of copper-free 3-((S)-1'-phenylethylamino)phenylamino-(amido)N-[3-((S)-1'-phenylethylamino)propyl]-belomycin. IR absorption maxima (wave number, cm$^{-1}$) as measured in KBr-tablet were 3370, 2975, 2940, 1715, 1660, 1565, 1500, 1455, 1385, 1320, 1255, 1190, 1140, 1100, 1060, 1020, 970, 920, 880, 805, 760, 730, and 695. Other physicochemical properties were as shown in Table 2.

In a manner similar to that described above, other compounds listed in step B were each converted into copper-free form. The physicochemical properties of these compounds were as shown in Table 2.

EXAMPLE 4

A solution of 10.22 g of 3-aminopropyldimethylamine in 100 ml of methanol was neutralized with 12 ml of glacial acetic acid and mixed with 100 g of benzaldehyde. To the stirred mixture, was added portionwise 8.38 g of sodium cyanoborohydride. The mixture was allowed to react at room temperature for 16 hours. The reaction mixture was adjusted to pH 1 with concentrated hydrochloric acid, and stripped of the methanol by distillation under reduced pressure. The residue was treated with 200 ml of water and 200 ml of chloroform. The aqueous layer was separated and extracted with 200 ml of chloroform to remove the benzaldehyde. The aqueous layer was adjusted to pH 12 with sodium hydroxide and extracted twice with 200 ml of chloroform. The chloroform extract was dried over sodium sulfate and freed from the solvent by distillation under reduced pressure to yield 26 g (92% yield) of [3-(N,N-dimethylamino)propyl]dibenzylamine.

The amine obtained above was dissolved in 100 ml of acetonitrile. To the stirred solution, was added dropwise a solution of 22.25 g of N-(3-bromopropyl)phthalimide in 100 ml of acetonitrile. The mixture was stirred at room tmeperature for 18 hours until the halide had disappeared, as confirmed by thin layer chromatography. The reaction mixture was stripped of the acetonitrile by distillation under reduced pressure. The residue was dissolved in 200 ml of 6N hydrochloric acid and hydrolyzed by heating at 110° C. for 8 hours. The hydrolyzate solutoin was cooled, removed of the precipiated phthalic acid by filtation, evaporated to dryness, dissolved in distilled water, and passed through a column of an ion exchange resin Dowex®—1 (Cl type, 279 ml in volume). The effluent was evaporated to dryness under reduced pressure to yield 43.7 g of N-{3-[N-(3-aminopropyl)-N,N-dimethylamino]propyl}dibenzylamine trihydrochloride. The PMR spectrum of this compound, as determined in heavy water showed the following signals: $\delta$(ppm)=2.0–2.7, 4H (m); 2.9–3.8, 8H (m); 3.3, 6H (s); 4.6, 4H (m); 7.7, 10H (s) (wherein m and s in parentheses stand for multiplet and singlet, respectively). These signals are indicative of the chemical structure as given above. Other physicochemical properties were as shown in Table 8.

In a manner similar to that described above, N-{3-[N-(3-aminopropyl)-N,N-diethylamino]propyl}dibenzylamine trihydrochloride was obtained from 3-aminopropyldiethylamine used as starting material. The physicochemical properties were as shown in Table 8.

EXAMPLE 5

Into 180 ml of water, was dissolved 150 g of bis(3-aminopropyl)methylamine followed by 53 g of triethylamine. To the solution, while being cooled in ice and stirred, was added portionwise a solution of 83 g ($\frac{1}{3}$ equivalent) of 4,6-dimethyl-2-tert-butoxycarbonylthiopyrimidine in 200 ml of dioxane. The mixture was allowed to react at room temperature for 5 hours. The reaction mixture was stripped of the dioxane and triethyl amine by disillation under reduced pressure. The residue was adjusted to pH 2 with 6N hydrochloric acid and washed with chloroform. The aqueous layer was adjusted to pH 13.5 with sodium hydroxide and extracted with chloroform. The chloroform layer was dried over sodium sulfate and freed from the solvent by distillation under reduced pressure to yield 60 g (24% yield) of (3-tert-butoxycarbonylaminopropyl)-(3-aminopropyl)methylamine (BOC-APMP).

Into 130 ml of methanol, was dissolved the BOC-APMP obtained above. To the solution, while being cooled in ice and stirred, were added 69 g (2 equivalents) of cyclooctanecarboxyaldehyde and a solution of 10 g of sodium cyanoborohydride (NaBH$_3$CN) in 20 ml of methanol. The mixture was stirred at room temperature for 24 hours. After completion of the reaction, 30 ml of 6N hydrochloric acid was added to the reaction mixture to decompose the excess reducing agent as well as to remove the tert-butoxy group. The mixture was stripped of the methanol by distillation under reduced pressure, admixed with 400 ml of distilled water, and extracted with 300 ml of chloroform to remove the residual aldehyde. The aqueous layer was adjusted to pH 13.5 with sodium hydroxide and extracted twice with 200 ml of chloroform. The chloroform layer containing the intended product was dried over sodium sulfate and stripped of the chloroform by distillation under reduced pressure. The residue was mixed with 100 ml of distilled water and 50 ml of concentrated hydrochloric acid and evaporated to dryness to yield 66 g (71% yield) of N-{3-[N-(3-aminopropyl)-N-methylamino]propyl}cyclooctylamine trihydrochloride.

PMR spectrum of the above product as determined in heavy water showed the following signals: $\delta$(ppm)=1.2–2.3, 15H (m); 2.0–2.8, 4H (m), 3.0–3.9, 10H (m); 3.25, 3H (s) (wherein m and s are as defined above). These signals indicate the chemical structure of the compound to be as given above. Other physicochemical properties were as shown in Table 8.

In a similar manner to that described above, N-{3-[N-(3-aminopropyl)-N-methylamino]propyl}-p-cyanobenzylamine trihydrochloride (81% yeild) and N-{3-[N-(3-aminopropyl)-N-metylamino]propyl}-2-(p-chlorophenyl)ethylamine trihydrochloride (51% yield) were obtained from p-cyanobenzaldehyde and p-chlorophenylacetaldehyde, respectively. The physicohemical properties of these compounds were as shown in Table 8.

EXAMPLE 6

A solution of 14.90 g of BOC-APMP obtained in the first step of Example 5 in 300 ml of methanol was adjusted to pH 6.4 with glacial acetic acid. To the solution cooled in ice, 77.30 g (4 equivalents) of 3,4-dibenzyloxybenzaldehyde followed by 5.0 g of NaBH$_3$CN. The mixture was brought to room temperature, then stirred for 96 hours, and stripped of the methanol by distillation under reduced pressure. The residue was diluted with 200 ml of distilled water and extracted twice with each 200 ml of chloroform. The chloroform layers were combined, dried over sodium sulfate, concentrated to 100 ml, and passed through a silica gel column, 1,200 ml in volume, which had been washed with chloroform in advance, to effect adsorption of the intended compound onto the column. The adsorbed phase was eluted with a chloroform-methanol mixture while increasing stepwise the methanol concentration. The intended product was eluted at the stage in which the chloroform-to-methanol ratio reached 97:3. The eluate fractions containing the intended product were combined and concentrated under reduced pressure to obtain 31.43 g of 1-[N-(3-tert-butoxycarbonylaminopropyl)-N-methylamino]-3-[bis(3,4-dibenzyloxybenzyl)amino]propane in an oily form. To a solution of the oil in 78.6 ml of dichloromethane, while being cooled in ice and stirred, was added 78.6 ml of trifluoroacetic acid (TFA) dropwise over a period of 30 minutes. The mixture was allowed to react for 1.5 hours at 0° C. The bath temperature was then elevated to 25° C. and the solvent was distilled off under reduced pressure. The residue was mixed with 200 ml of distilled water and 50 ml of 5N aqueous sodium hydroxide solution, and extracted with 500 ml of chloroform to collect 3-{N-{N-methyl-N-[3'-bis(m,p-dibenzyloxybenzyl)aminopropyl]amino}}propylamine to give 21.08 g (46.2% yield) of MDD-amine (free base) in the form of oil. The physicochemical properties were as shown in Table 8.

TABLE 8

| Synthesized amine | IR (cm$^{-1}$) (KBr-tablet) | PMR*$^1$ (ppm) (60 MHz, D20) | | Rm*$^2$ | Rf*$^3$ |
|---|---|---|---|---|---|
| N—{3-[N—(3-aminopropyl)-N,N—dimethylamino]propyl}-dibenzylamine trihydrochloride | 3425, 2975, 2750, 2600, 2000, 1640, 1600, 1480, 1460, 1420, 1350, 1300, 1220, 1190, 1160, 1120, 1060, 1030, 960, 920, 850, 700 | 2.0–2.7<br>2.9–3.8<br>3.3<br>4.6<br>7.7 | 4 H (m)<br>8 H (m)<br>6 H (s)<br>4 H (m)<br>10 H (s) | 1.32 | 0.72 |
| N—{3-[N—(3-aminopropyl)-N,N—diethylamino]propyl}-dibenzylamine trihydrochloride | 3425, 2975, 2750, 2600, 2000, 1600, 1480, 1450, 1400, 1200, 1180, 1160, 1120, 1080, 1050, 1020, 990, 960, 900, 800, 740, 680 | 1.4<br>1.9–2.6<br>4.7<br>7.7 | 6 H (t)<br>4 H (m)<br>4 H (s)<br>10 H (s) | 1.64 | 0.81 |
| N—{3-[N—(3-aminopropyl)-N—methylamino]propyl}-cyclooctylmethylamine trihydrochloride | 3425, 2950, 2875, 2775, 2700, 2050, 1600, 1480, 1300, 1200, 1170, 1140, 1070, 990, 970, 950, 850, 770 | 1.2–2.3<br>2.0–2.8<br>3.0–3.9<br>3.25 | 15 H (m)<br>4 H (m)<br>10 H (m)<br>3 H (m) | 1.77 | 0.30 |
| N—{3-[N—(3-aminopropyl)-N—methylamino]propyl}-(p-cyanobenzyl)amine trihydrochloride | 3425, 2975, 2800, 2750, 2675, 2250, 2000, 1960, 1840, 1700, 1600, 1520, 1300, 1220, 1170, 1120, 1060, 1030, 990, 970, 900, 860, 830, 760 | 2.0–2.7<br>3.0–3.8<br>3.1<br>4.5<br>7.7–8.1 | 4 H (m)<br>8 H (m)<br>3 H (s)<br>2 H (s)<br>4 H (m) | 1.86 | 0.38 |
| N—{3-[N—(3-aminopropyl)-N—methylamino]propyl}-2-(p-chlorophenyl)ethylamine trihydrochloride | 3425, 2975, 2800, 2650, 2500, 2000, 1600, 1500, 1460, 1410, 1310, 1200, 1160, 1100, 1070, 1027, 960, 860, 810, 760, 720, 650 | 2.1–2.8<br>2.9–3.9<br>3.2<br>7.4–7.8 | 4 H (m)<br>12 H (m)<br>3 H (s)<br>4 H (m) | 1.78 | 0.27 |
| 3-{N—{N—methyl-N—[3-bis(m,p-dibenzyloxybenzyl)aminopropyl]amino}}propylamine | 690, 730, 790, 805, 850, 905, 1020, 1085, 1130, 1160, 1195, 1220, 1265, 1380, 1425, 1455, 1510, 1590, 1610, 1650, 1760, 1815, 1880, 1960, 2800, 2870, 2940, 3040, 3075, 3375, 3660 | 1.2–1.9<br>2.0–2.9<br>3.43<br>5.16<br>6.6–7.7 | 6 H (m)<br>11 H (m)<br>4 H (s)<br>8 H (s)<br>26 H (m) | 0.78 | 0.24*$^4$ |

Note:
*$^1$m, t, and m in parentheses stand for singlet, triplet and multiplet, respectively.
*$^2$Relative mobility when that of alanine is 1.0 in the thin layer electrophoresis [Avicel SF ® (FMC Co.), formic acid-acetic acid-water (27:75:900 v/v), 800 V, 6 minutes].
*$^3$Thin layer chromatography: Silica Gel 60F 254 (Merck Co.), methanol-10% aqueous ammonium acetate solution-10% aqueous ammonia (1:1:1 v/v), ninhydrin color reaction.
*$^4$Methanol-10% aqueous ammonium acetate solution-10% aqueous ammonia (10:1:1 v/v)

(briefly MDD-amine). The aqueous layer was again extracted with 100 ml of chloroform. The chloroform layers were combined, dried over sodium sulfate, and stripped of the chloroform under reduced pressure, to given 26.30 g of a crude oil of MDD-amine. For the purpose of purification, the crude oil was subjected to Amberlite ®XAD-2 (2,000 ml in volume) column chromatography which was carried out in the following way. The crude oil was dissolved in 75 ml of methanol and the solution was mixed with 750 ml of a 4-% aqueous potassium acetate solution-2-% aqueous acetic acid (1:1) buffer solution. The resulting suspension was passed through the said column to adsorb the intended product onto the column. The said buffer solution was allowed to flow through the column and methanol was added to the buffer so as to increase stepwise the methanol concentration. The intended product (MDD-amine) was found to be eluted when the buffer-to-methanol ratio became 15:85. The fraction containing the intended product was stripped of the methanol by distillation under reduced pressure, then adjusted to pH 13 with 5N aqueous sodium hydroxide solution, and extracted three times with each 300 ml of chloroform. The chloroform layers were combined, dried over sodium sulfate, stripped of the chloroform by distillation under reduced pressure, and dried over phosphorus pentoxide

What is claimed is:
1. An (amido)N-substituted bleomycin, or a salt thereof, represented by the following general formula:

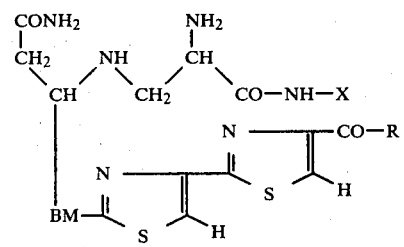

wherein BM represents a moiety of bleomycin skeleton; X represents (1) an alkyl of 1 to 18 carbon atoms, (2) an aminoalkyl of 1 to 12 carbon atoms, (3) a lower alkyl having as substituent(s) (a) 1 to 3 halogen atoms, (b) 1 or 2 phenyl groups which may be substituted by a halogen atom, (c) an indolyl group which may be substituted by a lower alkoxy group, or (d) a furyl group, a pyridyl group, a thiazolyl group or a piperidyl group, (4) $X_1$-(lower)alkyl where $X_1$ is

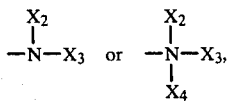

$X_2$ is a hydrogen atom, a lower alkyl or benzyl, $X_3$ is (a) a lower alkyl, (b) a phenyl(lower)alkyl, or (c) a mono or di-(lower)alkylamino(lower)alkyl which may be substituted by a phenyl or halophenyl group, $X_4$ is (a) a lower alkyl or (b) a phenyl(lower)alkyl, (5) naphthyl, or (6) an N-phenyl(lower)alkylpiperidyl; and R represents a terminal amino residue of the bleomycin.

2. An (amido)N-substituted bleomycin or a salt thereof according to claim 1, wherein X of the general formula is an alkyl of 1 to 12 carbon atoms or a lower alkyl having as substituent (a) 1 to 3 halogen atoms, (b) 1 or 2 phenyl groups, (c) an indolyl group, or (d) a 5- or 6-membered heterocyclic group containing a sulfur or nitrogen atom (among the substituent groups, the phenyl or indolyl group may be further substituted by a halogen atom or a lower alkoxy group).

3. An (amido)N-substituted bleomycin or a salt thereof according to claim 1, wherein X of the general formula is an alkyl of 1 to 12 carbon atoms, a trihalo(lower)alkyl, an aminoalkyl of 2 to 12 carbon atoms, a phenyl lower alkyl, a halophenyl(lower)alkyl, a diphenyl(lower)alkyl, a methoxyindolyl, a pyridyl(lower)alkyl, a piperazinyl(lower)alkyl, an $X_1$-(lower)alkyl [where $X_1$ is

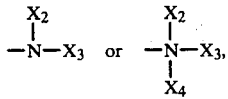

$X_2$ is a hydrogen atom, a lower alkyl or benzyl, $X_3$ is (a) a lower alkyl, (b) a phenyl(lower)alkyl, or (c) a mono- or di-(lower)alkylamino(lower)alkyl which may be substituted by a phenyl or halophenyl group, and $X_4$ is (a) a lower alkyl or (b) a phenyl(lower)alkyl], a thiazolyl, or an N-phenyl(lower)alkylpiperzinyl.

4. An (amido)N-substituted bleomycin or a salt thereof according to claim 1, wherein the $X_1$-(lower)alkyl is a mono- or di-(lower)alkylamino(lower)alkylamino(lower)alkyl, a phenyl(lower)alkylamino(lower)alkyl, a di(lower)alkylamino(lower)alkyl, an N-[halophenyl(lower)alkylamino(lower)alkyl]-N-(lower)alkylamino(lower)alkyl, or an N-(lower)alkyl-N-phenyl(lower)alkyl-N-[diphenyl(lower)alkylamino(lower)alkyl]amino(lower)alkyl.

5. An (amido)N-substituted bleomycin or a salt thereof according to claim 1, wherein R is an aliphatic primary amino group having a basic group.

6. An (amido)N-substituted bleomycin or a salt thereof according to claim 5, wherein the aliphatic primary amino group is 1-phenylethylaminopropylamino group, butylaminopropylamino group, or a group of the formula —NH(CH$_2$)$_3$—A'—(CH$_2$)$_3$—B' {where A' is

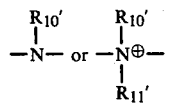

(where $R_{10}'$ is a lower alkyl and $R_{11}'$ is a lower alkyl or benzyl) and B' is

[where $R_{12}'$ is a phenyl(lower)alkyl which may have on its phenyl group one or more (a) halogen atoms, (b) cyano groups, or (c) benzyloxy groups, or a lower alkyl substituted by a cycloalkyl group of 5 to 13 carbon atoms; and $R_{13}'$ is a hydrogen atom or benzyl group which may be substituted by 1 or 2 benzyloxy groups]}.

7. An (amido)N-substituted bleomycin or a salt thereof according to claim 1, wherein X is isopropyl, 1-phenylethylaminopropyl, diethylamino-1-methylbutyl, or dibutylaminopropyl and R is 1-phenylethylaminopropylamino, an N-(lower)alkyl-N-(halobenzylaminopropyl)amino propylamino, or n-butylaminopropylaminopropylamino.

8. An (amido)N-substituted bleomycin or a salt thereof according to claim 1, wherein X is an alkyl of 3 to 10 carbon atoms, benzyl, 1-phenylethylaminopropyl, di-n-butylaminopropyl, n-butylaminopropylaminopropyl, N-methyl-N-benzyl-N-(dibenzylaminopropyl)aminopropyl, or N-methyl-N-(halophenylethylaminopropyl)aminopropyl and R is N-methyl-N-(halophenylethylaminopropyl)aminopropylamino, N-methyl-N-benzyl-N-(dibenzylaminopropyl)aminopropylamino, N-methyl-N-[bis(m,p-dibenzyloxybenzyl)aminopropyl]aminopropylamino, N,N-dimethyl-N-(dibenzylaminopropyl)aminopropylamino, N,N-diethyl-N-(dibenzylaminopropyl)aminopropylamino, N-methyl-N-(cyclooctylmethylaminopropyl)aminopropylamino, or N-methyl-N-(cyanobenzylaminopropyl)aminopropylamino.

9. 3-{N,N-dimethyl-N-[3-(dibenzylamino)propyl]amino}propylamino-(amido)N-[3-((S)-1'-phenylethyl)aminopropyl]bleomycin or a salt thereof.

10. 3-{N-methyl-N-[3'-bis(m,p-dibenzyloxybenzyl)aminopropyl]amino}propylamino-(amido)-N-[3-((S)-1'-phenylethyl)aminopropyl]bleomycin or a salt thereof.

11. 3-{N,N-dimethyl-N-[3-(dibenzylamino)propyl]amino}propylamino-(amido)N-octylbleomycin.

12. 3-{N-methyl-N-[3'-bis(m,p-dibenzyloxybenzyl)aminopropyl]amino}propylamino-(amido)N-octylbleomycin.

* * * * *